United States Patent
Béliveau et al.

(10) Patent No.: US 9,334,314 B2
(45) Date of Patent: May 10, 2016

(54) PEPTIDE COMPOUNDS DERIVED FROM MELANOTRANSFERRIN AND USES THEREOF

(71) Applicant: Theratechnologies Inc., Montreal, Quebec (CA)

(72) Inventors: Richard Béliveau, Ile-des-Soeurs (CA); Jonathan Michaud-Levesque, Montreal (CA); Krishna G. Peri, Ville Saint-Laurent (CA); Abdelkrim Habi, Pierrefonds (CA); Nathalie Bousquet-Gagnon, Mirabel (CA)

(73) Assignee: THERATECHNOLOGIES INC., Montreal (CA)

( * ) Notice: Subject to any disclaimer, the term of this patent is extended or adjusted under 35 U.S.C. 154(b) by 0 days.

(21) Appl. No.: 14/352,600

(22) PCT Filed: Oct. 18, 2012

(86) PCT No.: PCT/CA2012/050741
§ 371 (c)(1),
(2) Date: Apr. 17, 2014

(87) PCT Pub. No.: WO2013/056372
PCT Pub. Date: Apr. 25, 2013

(65) Prior Publication Data
US 2015/0133385 A1    May 14, 2015

Related U.S. Application Data

(60) Provisional application No. 61/548,905, filed on Oct. 19, 2011.

(51) Int. Cl.
*C07K 7/08* (2006.01)
*C07K 14/47* (2006.01)
*C07K 14/79* (2006.01)
*A61K 38/40* (2006.01)

(52) U.S. Cl.
CPC . *C07K 14/47* (2013.01); *C07K 7/08* (2013.01); *C07K 14/79* (2013.01); *A61K 38/40* (2013.01)

(58) Field of Classification Search
None
See application file for complete search history.

(56) References Cited

U.S. PATENT DOCUMENTS

| | | | |
|---|---|---|---|
| 7,919,103 B2 * | 4/2011 | Beliveau et al. | 424/198.1 |
| 2004/0055022 A1 * | 3/2004 | Cheng et al. | 800/3 |
| 2007/0053894 A1 * | 3/2007 | Beliveau et al. | 424/94.2 |
| 2011/0243952 A1 | 10/2011 | Beliveau et al. | |
| 2013/0058873 A1 * | 3/2013 | Jefferies et al. | 424/9.34 |

FOREIGN PATENT DOCUMENTS

| | | |
|---|---|---|
| EP | 12841071.9 | 4/2015 |
| WO | WO2010034490 | 4/2010 |
| WO | PCT/CA2012/050741 | 1/2013 |
| WO | PCT/CA2012/050741 | 5/2014 |

OTHER PUBLICATIONS

Demeule et al ('Regulation of plasminogen activation: a role for melanotransferrin (p97) in cell migratation' Blood v102(5) Sep. 1, 2003 pp. 1723-1731, printed as 18 pages).*
Andreasen et al., The urokinase-type plasminogen activator system in cancer metastasis: a review, Int. J. Cancer:72, 1-22 (1997).
Andreasen et al., The plasminogen activation system in tumor growth, invasion, and metastasis, CMLS Cell. Mol. Life Sci:57, 25-40 (2000).
Brown et al., Quantitative analysis of melanoma-associated antigen p97 in normal and neoplastic tissues, Proc. Natl. Acad. Sci. USA:78, 539-575 (1981).
Brown et al., Structural characterization of human melanoma-associated antigen p97 with monoclonal antibodies, J. Immunol:127, 539-546 (1981).
Brown et al., Human melanoma-associated antigen p97 is structurally and functionally related to transferrin, Nature:296, 171-173 (1982).
Choong et al., Urokinase plasminogen activator system, Clinical Orthopaedics and related research:415S, S46-S58 (2003).
Demeule et al., Regulation of plasminogen activation: a role for melanotransferrin (p97) in cell migration, Blood:102, 1723-1731 (2003).
Michaud-Levesque et al., Stimulation of cell surface plasminogen activation by membrane-bound melanotransferrin: A key phenomenon for cell invasion, Experimental Cell Research:308, 479-490 (2005).
Michaud-Levesque et al., Inhibition of endothelial cell movement and tubulogenesis by human recombinant soluble melanotransferrin: involvement of the u-PAR/LRP plasminolytic system, Biochimica et Biophysica Acta:1743, 243-253 (2005).
Michaud-Levesque et al., In vivo inhibition of angiogenesis by a soluble form of melanotransferrin, Carcininogenesis:28, 280-288 (2007).
Montgomery et al., Melanoma-mediated dissolution of extracellular matrix: contribution of urokinase-dependent and metalloproteinase-dependent proteolytic pathways, Cancer Res:53, 693-700 (1993).
Rolland et al., Inhibition of tumor growth by a truncated and soluble form of melanotransferrin, Experimental Cell Research:313, 2910-2919 (2007).
Stahl et al., Binding of urokinase to its receptor promotes migration and invasion of human melanoma cells in vitro, C Cancer Res:54, 3066-3071 (1994).
Woodbury et al., Identification of a cell surface protein, p97, in human melanomas and certain other neoplasms, Proc. Natl. Acad. Sci. USA:77, 2183-2187 (1980).

* cited by examiner

*Primary Examiner* — Karlheinz R Skowronek
*Assistant Examiner* — Ronald Niebauer
(74) *Attorney, Agent, or Firm* — Fish & Richardson P.C.

(57) ABSTRACT

Peptide compounds derived from human melanotransferrin, and compositions thereof, are described. Uses of these peptide compounds, for example to modulate angiogenesis and/or cell migration, and/or to treat angiogenesis-related disorders (e.g., cancer), are also described.

9 Claims, 12 Drawing Sheets

NCI-H460 xenograft

| Molecule | Dosage (mg/Kg/day) | Tumor volume (mm³) Initial | Tumor volume (mm³) Final | ΔC/ΔT (%) |
|---|---|---|---|---|
| sMTf | 0 | 71+/-29 | 642+/-240 | 100 |
|  | 2.5 | 69+/-26 | 140+/-69 | 12.4 |
|  | 10 | 49+/-15 | 65+/-32 | 2.8 |
| SEQ ID No. 10 | 0 | 68+/-30 | 680+/-374 | 100 |
|  | 40 | 59+/-12 | 248+/-85 | 31 |

NCI-H460 xenograft

| Molecule | Dosage (mg/Kg/day) | Tumor volume (mm³) Initial | Tumor volume (mm³) Final | ΔC/ΔT (%) |
|---|---|---|---|---|
| sMTf | 0 | 71+/-29 | 642+/-240 | 100 |
|  | 2.5 | 69+/-26 | 140+/-69 | 12.4 |
|  | 10 | 49+/-15 | 65+/-32 | 2.8 |
| SEQ ID No. 5 | 0 | 42+/-13 | 445+/-516 | 100 |
|  | 40 | 38+/-10 | 259+/-96 | 54.7 |
| SEQ ID No. 7 | 0 | 42+/-13 | 445+/-516 | 100 |
|  | 40 | 29+/-4 | 356+/-192 | 81.2 |

NCI-H460 xenograft

| Molecule | Dosage (mg/Kg/day) | Tumor volume (mm³) Initial | Tumor volume (mm³) Final | ΔC/ΔT (%) |
|---|---|---|---|---|
| sMTf | 0 | 71+/-29 | 642+/-240 | 100 |
|  | 2.5 | 69+/-26 | 140+/-69 | 12.4 |
|  | 10 | 49+/-15 | 65+/-32 | 2.8 |
| SEQ ID No. 13 | 0 | 36+/-8 | 443+/-404 | 100 |
|  | 40 | 44+/-22 | 487+/-294 | 109.0 |
| SEQ ID No. 15 | 0 | 36+/-8 | 443+/-404 | 100 |
|  | 40 | 28+/-11 | 286+/-93 | 63.5 |
| SEQ ID No. 9 | 0 | 36+/-8 | 443+/-404 | 100 |
|  | 40 | 40+/-20 | 274+/-198 | 57,7 |

FIG. 5A

U87 xenograft

| Molecule | Dosage (mg/Kg/day) | Tumor volume (mm³) Initial | Tumor volume (mm³) Final | ΔC/ΔT (%) |
|---|---|---|---|---|
| sMTf | 0 | 71+/-29 | 642+/-240 | 100 |
|  | 2.5 | 69+/-26 | 140+/-69 | 12.4 |
|  | 10 | 49+/-15 | 65+/-32 | 2.8 |
| SEQ ID No. 5 | 0 | 66+/-19 | 535+/-302 | 100 |
|  | 40 | 64+/-14 | 351+/-127 | 61.2 |
| SEQ ID No. 7 | 0 | 66+/-19 | 535+/-302 | 100 |
|  | 40 | 59+/-21 | 623+/-176 | 120.3 |

U87 xenograft

| Molecule | Dosage (mg/Kg/day) | Tumor volume (mm³) Initial | Tumor volume (mm³) Final | ΔC/ΔT (%) |
|---|---|---|---|---|
| sMTf | 0 | 71+/-29 | 642+/-240 | 100 |
|  | 2.5 | 69+/-26 | 140+/-69 | 12.4 |
|  | 10 | 49+/-15 | 65+/-32 | 2.8 |
| SEQ ID No. 13 | 0 | 55+/-22 | 583+/-197 | 100 |
|  | 40 | 72+/-33 | 548+/-210 | 90.6 |
| SEQ ID No. 15 | 0 | 55+/-22 | 583+/-197 | 100 |
|  | 40 | 69+/-14 | 204+/-51 | 25.6 |

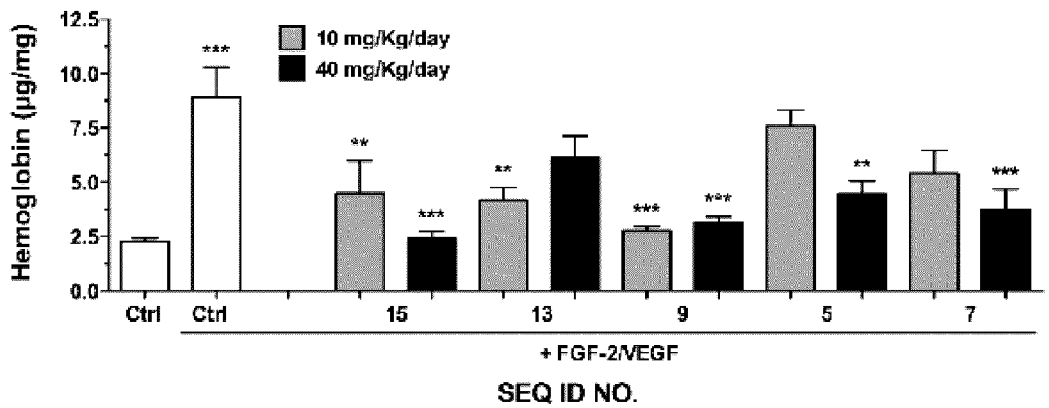

FIG. 7

Amino acid sequence of human melanotransferrin (SEQ ID NO: 1)

```
MRGPSGALWLLLALRTVLGGMEVRWCATSDPEQHKCGNMSEAFREAGIQPSLLCVRGTSA
DHCVQLIAAQEADAITLDGGAIYEAGKEHGLKPVVGEVYDQEVGTSYYAVAVVRRSSHVT
IDTLKGVKSCHTGINRTVGWNVPVGYLVESGRLSVMGCDVLKAVSDYFGGSCVPGAGETS
YSESLCRLCRGDSSGEGVCDKSPLERYYDYSGAFRCLAEGAGDVAFVKHSTVLENTDGKT
LPSWGQALLSQDFELLCRDGSRADVTEWRQCHLARVPAHAVVVRADTDGGLIFRLLNEGQ
RLFSHEGSSFQMFSSEAYGQKDLLFKDSTSELVPIATQTYEAWLGHEYLHAMKGLLCDPN
RLPPYLRWCVLSTPEIQKCGDMAVAFRRQRLKPEIQCVSAKSPQHCMERIQAEQVDAVTL
SGEDIYTAGKTYGLVPAAGEHYAPEDSSNSYYVVAVVRRDSSHAFTLDELRGKRSCHAGF
GSPAGWDVPVGALIQRGFIRPKDCDVLTAVSEFFNASCVPVNNPKNYPSSLCALCVGDEQ
GRNKCVGNSQERYYGYRGAFRCLVENAGDVAFVRHTTVFDNTNGHNSEPWAAELRSEDYE
LLCPNGARAEVSQFAACNLAQIPPHAVMVRPDTNIFTVYGLLDKAQDLFGDDHNKNGFKM
FDSSNYHGQDLLFKDATVRAVPVGEKTTYRGWLGLDYVAALEGMSSQQCSGAAAPAPGAP
LLPLLLPALAARLLPPAL
```

FIG. 8

```
23-355      RWCATSDPEQHKCGNMSEAFREAGIQPSLLCVRGTSADHCVQLIAAQEADAITLDGGAIY  83
Consensus   RWC   S PE   KCG+M+ AFR    ++P + CV    S   HC++ I  A++ DA+TL G   IY
367-706     RWCVLSTPEIQKCGDMAVAFRRQRLKPEIQCVSAKSPQHCMERIQAEQVDAVTLSGEDIY
427

23-355      EAGKEHGLKPVVGEVY-DQEVGTSYYAVAVVRR-SSHV-TIDTLKGVKSCHTGINRTVGW
140
Consensus    AGK +GL P  GE Y  ++   SYY VAVVRR SSH   T+D L+G +SCH  G      GW
367-706     TAGKTYGLVPAAGEHYAPEDSSNSYYVVAVVRRDSSHAFTLDELRGKRSCHAGFGSPAGW
487

23-355      NVPVGYLVESGRLSVMGCDVLKAVSDYFGGSCVPGAGETSYSESLCRLCRGDSSGEGVCD
200
Consensus   +VPVG L++ G +    CDVL AVS++F  SCVP     +Y  SLC LC GD  G    C
367-706     DVPVGALIQRGFIRPKDCDVLTAVSEFFNASCVPVNNPKNYPSSLCALCVGDEQGRNKCV
547

23-355      KSPLERYYDYSGAFRCLAEGAGDVAFVKHSTVLENTDGKTLPSWGQALLSQDFELLCRDG
260
Consensus    +  ERYY Y GAFRCL E AGDVAFV+H+TV +NT+G    W   L S+D+ELLC +G
367-706     GNSQERYYGYRGAFRCLVENAGDVAFVRHTTVFDNTNGHNSEPWAAELRSEDYELLCPNG
607

23-355      SRADVTEWRQCHLARVPAHAVVVRADTDGGLIFRLLNEGQRLF--SHEGSSFQMFSSEAY
318
Consensus   +RA+V+++  C+LA++P HAV+VR DT+    ++ LL++ Q LF   H + F+MF S  Y
367-706     ARAEVSQFAACNLAQIPPHAVMVRPDTNIFTVYGLLDKAQDLFGDDHNKNGFKMFDSSNY
667

23-355      GQKDLLFKDSTSELVPIATQ-TYEAWLGHEYLHAMKGL   355 (SEQ ID NO:32)
Consensus     +DLLFKD+T   VP+ +  TY WLG +Y+ A++G+
367-706     HGQDLLFKDATVRAVPVGEKTTYRGWLGLDYVAALEGM   705 (SEQ ID NO:33)

Score =  330 bits (847),  Expect = 2e-95, Method: Compositional matrix
adjust.
Identities = 163/338 (48%),  Positives = 219/338 (65%), Gaps = 6/338 (2%)
```

FIG. 9

Nucleic acid sequence encoding human melanotransferrin (SEQ ID NO: 30)

```
   1 cacttaagga gctcgggcca gcgcgagggg gagcagggag gaagcccggc tgctgcggac
  61 ctcctcggac ccggacccag ccccagcccg gccccagcca gccccgacgg cgccatgcgg
 121 ggtccgagcg gggctctgtg gctgctcctg gctctgcgca ccgtgctcgg tggcatggag
 181 gtgcggtggt gcgccacctc ggacccagag cagcacaagt gcggcaacat gagcgaggcc
 241 ttccgggaag cgggcatcca gccctccctc ctctgcgtcc ggggcacctc cgccgaccac
 301 tgcgtccagc tcatcgcggc ccaggaggct gacgccatca tctggatgg aggagccatc
 361 tatgaggcgg gaaaggagca cggcctgaag ccggtggtgg cgaagtgta cgatcaagag
 421 gtcggtacct cctattacgc cgtggctgtg gtcaggagga gctcccatgt gaccattgac
 481 accctgaaag gcgtgaagtc ctgccacacg gcatcaatc gcacagtggg ctggaacgtg
 541 cccgtgggct acctggtgga gagcggccgc ctctcggtga tgggctgcga tgtactcaaa
 601 gctgtcagcg actatttttgg gggcagctgc gtcccggggg caggagagac cagttactct
 661 gagtccctct gtcgcctctg caggggtgac agctctgggg aaggggtgtg tgacaagagc
 721 cccctggaga gatactacga ctacagcggg gccttccggt gcctggcgga aggggcaggg
 781 gacgtggctt ttgtgaagca cagcacggta ctggagaaca cggatgggaa gacgcttccc
 841 tcctggggcc aggccctgct gtcacaggac ttcgagctgc tgtgccggga tggtagccgg
 901 gccgatgtca ccgagtggag gcagtgccat ctggcccggg tgcctgctca cgccgtggtg
 961 gtccgggccg acacagatgg gggcctcatc ttccggctgc tcaacgaagg ccagcgtctg
1021 ttcagccacg agggcagcag cttccagatg ttcagctctg aggcctatgg ccagaaggat
1081 ctactcttca aagactctac ctcggagctt gtgcccatcg ccacacagac ctatgaggcg
1141 tggctgggcc atgagtacct gcacgccatg aagggtctgc tctgtgaccc caaccggctg
1201 cccccctacc tgcgctggtg tgtgctctcc actcccgaga tccagaagtg tggagacatg
1261 gccgtggcct tccgccggca gcggctcaag ccagagatcc agtgcgtgtc agccaagtcc
1321 ccccaacact gcatggagcg gatccaggct gagcaggtcg acgctgtgac cctgagtggc
1381 gaggacattt acacggcggg gaagacgtac ggcctggttc ccgcagccgg ggagcactat
1441 gccccggaag acagcagcaa ctcgtactac gtggtggccg tggtgagacg ggacagctcc
1501 cacgccttca ccttggatga gcttcgggc aagcgctcct gccacgccgg tttcggcagc
1561 cctgcaggct gggatgtccc cgtgggtgcc cttattcaga gaggcttcat ccggcccaag
1621 gactgtgacg tcctcacagc agtgagcgag ttcttcaatg ccagctgcgt gcccgtgaac
1681 aaccccaaga actacccctc ctcgctgtgt gcactgtgcg tggggacga gcagggccgc
1741 aacaagtgtg tgggcaacag ccaggagcgg tattacggct accgcggcgc cttcaggtgc
1801 ctggtggaga atgcgggtga cgttgccttc gtcaggcaca accgtctt tgacaacaca
1861 aacggccaca attccgagcc ctgggctgct gagctcaggt cagaggacta tgaactgctg
1921 tgccccaacg gggcccgagc cgaggtgtcc cagtttgcag cctgcaacct ggcacagata
1981 ccaccccacg ccgtgatggt ccggcccgac accaacatct tcaccgtgta tggactgctg
2041 gacaaggccc aggacctgtt tggagacgac cacaataaga cgggttcaa aatgttcgac
2101 tcctccaact atcatggcca agacctgctt ttcaaggatg ccaccgtccg ggcggtgcct
2161 gtcggagaga aaaccaccta ccgcggctgg ctggggctgg actacgtggc ggcgctggaa
2221 gggatgtcgt ctcagcagtg ctcgggcgca gcggccccgg cgcccgggc gcccctgctc
2281 ccgctgctgc tgcccgctct cgccgcccgc ctgctccgc ccgccctctg agcccggccg
2341 ccccgcccca gagctccgat gcccgcccgg ggagtttccg cggcggcttc gcgctggaat
2401 ccagaaggaa gctcgcgaag gccgggcccg gcgtgggcgg gagcaggcgc ctccccggga
2461 gccccgccgc ccacgggcgc cacctggcgc tgctacctga ggcgccgccc ccgggcccgc
2521 gcggcccttc ccgccaaccg ccgcctcccg ccacctggag ccgcgcgggc gcgccggag
2581 gaggccggtt gccaggaaa ccgctgagtc cgggcttccc gccgcccgcc ccgcggtgtc
2641 gcccgagggg cccgcccgcc tcctccccgc agccccgcgc cccgtccgc gaggcccct
2701 gggacgcgg tggccgccga ggcgcctaca cccgcaggcc gcggccaggc cgtcccagga
2761 ggccccggcg ccaacgggac ccggcgcgtg gacagcggc tctgctggc ggcggcggga
2821 gggaggccgg accggggcga cggggagaag ccttcgcccg cggaccgtg tccggggtgg
2881 gggctccagt tcctccgacc gcccgtgcgc tgggagggag gccgagcccg ggaacgccg
2941 cgtgccctgc ctcgtccccc actgtggccg cgccagctcc atcccgggcc agccgcgtcc
```

FIG. 10A

```
3001 acgggccccc tcccgagtct cctcaggctc tcgcctcccc taccccgtg ggatgcccac
3061 cgcccgcacc cacgcccgag cctggcggca gcagccgccc cccgcctgaa gggagccgga
3121 ggtgacccag gccgcgggct cccgaggccc ctgaagggct gcgcgtgggg acccgccatg
3181 cttctgggtt ccgaacgggg gtgagctccg tctcctcacc cggccccgca cccgctgggc
3241 ctggggaccc ctcactcccc gtgcccgccc ctccgcgagg cagcagaaag cgcccggccg
3301 gggcctctct ctactccatc ttgccacagt tgtctgagaa gccagaaaaa gtttccagaa
3361 ctggcagccc ttaaaaaaaa tgaagaggaa gagaagaaat gggagcaggc agccctcgtc
3421 agcagaccgg gagccgcgtg ggcgcggagc catttgcatt ccggtctgcg ggggctcggg
3481 gatgctggtg acaggcccgg ttcccggtgg ctcgccccca cctgcgggcg tcgggaagga
3541 tcccttccat ctctcagccg cagaggaggc cctggcagcg ccccggctgt agccatgcaa
3601 ccccgaggag tcccgggcac cttcacccca ccgggagggg ccacaaggac ctgggcctcg
3661 gccaccaagc tttgtcccct ctcgctgtgg ggggctagtg attctcctcc gacctgacga
3721 ttgcttggtt ttttcaaaag ggagttttgt gcggtgagaa gtgtgtttct gtgtggctaa
3781 ctctgggcta gcgtgccgtg gccattgaag gtgtggcctg cgtgggtgca gtgtaagtga
3841 cgctggattg tcaggtggca gcaggggacc cctgctgtgt cagtgctaat gaaacatgtt
3901 ggttggtttc taaataaag ccaaacaagc cagcacatgc agaggcttgg accctgatag
3961 aaa
```

FIG. 10B

SEQUENCE LISTING

<160> NUMBER OF SEQ ID NOS: 33

<210> SEQ ID NO 1
<211> LENGTH: 738
<212> TYPE: PRT

-continued

<213> ORGANISM: Homo sapiens

<400> SEQUENCE: 1

```
Met Arg Gly Pro Ser Gly Ala Leu Trp Leu Leu Ala Leu Arg Thr
 1               5                  10                  15
Val Leu Gly Gly Met Glu Val Arg Trp Cys Ala Thr Ser Asp Pro Glu
            20                  25                  30
Gln His Lys Cys Gly Asn Met Ser Glu Ala Phe Arg Glu Ala Gly Ile
        35                  40                  45
Gln Pro Ser Leu Leu Cys Val Arg Gly Thr Ser Ala Asp His Cys Val
    50                  55                  60
Gln Leu Ile Ala Ala Gln Glu Ala Asp Ala Ile Thr Leu Asp Gly Gly
65                  70                  75                  80
Ala Ile Tyr Glu Ala Gly Lys Glu His Gly Leu Lys Pro Val Val Gly
                85                  90                  95
Glu Val Tyr Asp Gln Glu Val Gly Thr Ser Tyr Tyr Ala Val Ala Val
            100                 105                 110
Val Arg Arg Ser Ser His Val Thr Ile Asp Thr Leu Lys Gly Val Lys
        115                 120                 125
Ser Cys His Thr Gly Ile Asn Arg Thr Val Gly Trp Asn Val Pro Val
130                 135                 140
Gly Tyr Leu Val Glu Ser Gly Arg Leu Ser Val Met Gly Cys Asp Val
145                 150                 155                 160
Leu Lys Ala Val Ser Asp Tyr Phe Gly Gly Ser Cys Val Pro Gly Ala
                165                 170                 175
Gly Glu Thr Ser Tyr Ser Glu Ser Leu Cys Arg Leu Cys Arg Gly Asp
            180                 185                 190
Ser Ser Gly Glu Gly Val Cys Asp Lys Ser Pro Leu Glu Arg Tyr Tyr
        195                 200                 205
Asp Tyr Ser Gly Ala Phe Arg Cys Leu Ala Glu Gly Ala Gly Asp Val
    210                 215                 220
Ala Phe Val Lys His Ser Thr Val Leu Glu Asn Thr Asp Gly Lys Thr
225                 230                 235                 240
Leu Pro Ser Trp Gly Gln Ala Leu Leu Ser Gln Asp Phe Glu Leu Leu
                245                 250                 255
Cys Arg Asp Gly Ser Arg Ala Asp Val Thr Glu Trp Arg Gln Cys His
            260                 265                 270
Leu Ala Arg Val Pro Ala His Ala Val Val Arg Ala Asp Thr Asp
        275                 280                 285
Gly Gly Leu Ile Phe Arg Leu Leu Asn Glu Gly Gln Arg Leu Phe Ser
    290                 295                 300
His Glu Gly Ser Ser Phe Gln Met Phe Ser Ser Glu Ala Tyr Gly Gln
305                 310                 315                 320
Lys Asp Leu Leu Phe Lys Asp Ser Thr Ser Glu Leu Val Pro Ile Ala
                325                 330                 335
Thr Gln Thr Tyr Glu Ala Trp Leu Gly His Glu Tyr Leu His Ala Met
            340                 345                 350
Lys Gly Leu Leu Cys Asp Pro Asn Arg Leu Pro Pro Tyr Leu Arg Trp
        355                 360                 365
Cys Val Leu Ser Thr Pro Glu Ile Gln Lys Cys Gly Asp Met Ala Val
    370                 375                 380
Ala Phe Arg Arg Gln Arg Leu Lys Pro Glu Ile Gln Cys Val Ser Ala
385                 390                 395                 400
```

```
Lys Ser Pro Gln His Cys Met Glu Arg Ile Gln Ala Glu Gln Val Asp
                405                 410                 415
Ala Val Thr Leu Ser Gly Glu Asp Ile Tyr Thr Ala Gly Lys Thr Tyr
            420                 425                 430
Gly Leu Val Pro Ala Ala Gly Glu His Tyr Ala Pro Glu Asp Ser Ser
        435                 440                 445
Asn Ser Tyr Tyr Val Ala Val Arg Arg Asp Ser Ser His Ala
    450                 455                 460
Phe Thr Leu Asp Glu Leu Arg Gly Lys Arg Ser Cys His Ala Gly Phe
465                 470                 475                 480
Gly Ser Pro Ala Gly Trp Asp Val Pro Val Gly Ala Leu Ile Gln Arg
                485                 490                 495
Gly Phe Ile Arg Pro Lys Asp Cys Asp Val Leu Thr Ala Val Ser Glu
            500                 505                 510
Phe Phe Asn Ala Ser Cys Val Pro Val Asn Asn Pro Lys Asn Tyr Pro
        515                 520                 525
Ser Ser Leu Cys Ala Leu Cys Val Gly Asp Glu Gln Gly Arg Asn Lys
    530                 535                 540
Cys Val Gly Asn Ser Gln Glu Arg Tyr Tyr Gly Tyr Arg Gly Ala Phe
545                 550                 555                 560
Arg Cys Leu Val Glu Asn Ala Gly Asp Val Ala Phe Val Arg His Thr
                565                 570                 575
Thr Val Phe Asp Asn Thr Asn Gly His Asn Ser Glu Pro Trp Ala Ala
            580                 585                 590
Glu Leu Arg Ser Glu Asp Tyr Glu Leu Leu Cys Pro Asn Gly Ala Arg
        595                 600                 605
Ala Glu Val Ser Gln Phe Ala Ala Cys Asn Leu Ala Gln Ile Pro Pro
    610                 615                 620
His Ala Val Met Val Arg Pro Asp Thr Asn Ile Phe Thr Val Tyr Gly
625                 630                 635                 640
Leu Leu Asp Lys Ala Gln Asp Leu Phe Gly Asp His Asn Lys Asn
                645                 650                 655
Gly Phe Lys Met Phe Asp Ser Ser Asn Tyr His Gly Gln Asp Leu Leu
            660                 665                 670
Phe Lys Asp Ala Thr Val Arg Ala Val Pro Val Gly Glu Lys Thr Thr
        675                 680                 685
Tyr Arg Gly Trp Leu Gly Leu Asp Tyr Val Ala Ala Leu Glu Gly Met
    690                 695                 700
Ser Ser Gln Gln Cys Ser Gly Ala Ala Ala Pro Ala Pro Gly Ala Pro
705                 710                 715                 720
Leu Leu Pro Leu Leu Leu Pro Ala Leu Ala Ala Arg Leu Leu Pro Pro
                725                 730                 735
Ala Leu

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
```

<223> OTHER INFORMATION: AMIDATION

<400> SEQUENCE: 2

Phe Arg Cys Leu Val Glu Asn Ala Gly Asp Val Ala Phe Val Arg His
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 3

Tyr Ser Gly Ala Phe Arg Cys Leu Ala Glu Gly Ala Gly Asp Val Ala
1               5                   10                  15

Phe Val Lys His
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 4

Tyr Arg Gly Ala Phe Arg Cys Leu Val Glu Asn Ala Gly Asp Val Ala
1               5                   10                  15

Phe Val Arg His
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: AMIDATION

<400> SEQUENCE: 5

Phe Arg Cys Leu Val Glu Asn Ala Gly Asp Val Ala Phe Val Arg His
1               5                   10                  15

Lys Lys Lys

```
<210> SEQ ID NO 6
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 6

Phe Arg Cys Leu Val Glu Asn Ala Gly Asp Val Gly Phe Val Arg His
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 7

Phe Arg Cys Leu Val Glu Asn Ala Gly Asp Val Pro Phe Val Arg His
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: AMIDATION

<400> SEQUENCE: 8

Phe Arg Cys Leu Val Glu Gln Ala Pro Asp Val Lys Phe Val Arg His
1               5                   10                  15

Lys Lys Lys

<210> SEQ ID NO 9
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (23)..(23)
<223> OTHER INFORMATION: AMIDATION
```

<400> SEQUENCE: 9

Tyr Ser Gly Ala Phe Arg Met Leu Ala Glu Gly Ala Gly Asp Val Ala
1               5                   10                  15
Phe Val Lys His Lys Lys Lys
            20

<210> SEQ ID NO 10
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION
<220> FEATURE:
<221> NAME/KEY: MISC_FEATURE
<222> LOCATION: (21)..(39)
<223> OTHER INFORMATION: residues 21 to 39 are C to N-terminal
<220> FEATURE:
<221> NAME/KEY: MOD_RES
<222> LOCATION: (39)..(39)
<223> OTHER INFORMATION: ACETYLATION

<400> SEQUENCE: 10

Phe Arg Cys Leu Val Glu Asn Ala Gly Asp Val Ala Phe Val Arg His
1               5                   10                  15
Lys Lys Lys Lys Lys Lys Lys His Arg Val Phe Ala Val Asp Gly Ala
            20                  25                  30
Asn Glu Val Leu Cys Arg Phe
            35

<210> SEQ ID NO 11
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa at position 1 is D-Phe
<220> FEATURE:
<221> NAME/KEY: MISC_FEATURE
<222> LOCATION: (2)..(2)
<223> OTHER INFORMATION: Xaa at position 2 is D-Arg
<220> FEATURE:
<221> NAME/KEY: MISC_FEATURE
<222> LOCATION: (3)..(3)
<223> OTHER INFORMATION: Xaa at position 3 is D-Cys
<220> FEATURE:
<221> NAME/KEY: MISC_FEATURE
<222> LOCATION: (4)..(4)
<223> OTHER INFORMATION: Xaa at position 4 is D-Leu
<220> FEATURE:
<221> NAME/KEY: MISC_FEATURE
<222> LOCATION: (5)..(5)
<223> OTHER INFORMATION: Xaa at position 5 is D-Val
<220> FEATURE:
<221> NAME/KEY: MISC_FEATURE
<222> LOCATION: (6)..(6)
<223> OTHER INFORMATION: Xaa at position 6 is D-Glu

```
<220> FEATURE:
<221> NAME/KEY: MISC_FEATURE
<222> LOCATION: (7)..(7)
<223> OTHER INFORMATION: Xaa at position 7 is D-Asn
<220> FEATURE:
<221> NAME/KEY: MISC_FEATURE
<222> LOCATION: (8)..(8)
<223> OTHER INFORMATION: Xaa at position 8 is D-Ala
<220> FEATURE:
<221> NAME/KEY: MISC_FEATURE
<222> LOCATION: (10)..(10)
<223> OTHER INFORMATION: Xaa at position 10 is D-Asp
<220> FEATURE:
<221> NAME/KEY: MISC_FEATURE
<222> LOCATION: (11)..(11)
<223> OTHER INFORMATION: Xaa at position 11 is D-Val
<220> FEATURE:
<221> NAME/KEY: MISC_FEATURE
<222> LOCATION: (12)..(12)
<223> OTHER INFORMATION: Xaa at position 12 is D-Ala
<220> FEATURE:
<221> NAME/KEY: MISC_FEATURE
<222> LOCATION: (13)..(13)
<223> OTHER INFORMATION: Xaa at position 13 is D-Phe
<220> FEATURE:
<221> NAME/KEY: MISC_FEATURE
<222> LOCATION: (14)..(14)
<223> OTHER INFORMATION: Xaa at position 14 is D-Val
<220> FEATURE:
<221> NAME/KEY: MISC_FEATURE
<222> LOCATION: (15)..(15)
<223> OTHER INFORMATION: Xaa at position 15 is D-Arg
<220> FEATURE:
<221> NAME/KEY: MISC_FEATURE
<222> LOCATION: (16)..(16)
<223> OTHER INFORMATION: Xaa at position 16 is D-His
<220> FEATURE:
<221> NAME/KEY: MISC_FEATURE
<222> LOCATION: (17)..(19)
<223> OTHER INFORMATION: Xaa at positions 17 to 19 is D-Lys
<220> FEATURE:
<221> NAME/KEY: MOD_RES
<222> LOCATION: (19)..(19)
<223> OTHER INFORMATION: AMIDATION

<400> SEQUENCE: 11

Xaa Xaa Xaa Xaa Xaa Xaa Xaa Xaa Gly Xaa Xaa Xaa Xaa Xaa Xaa Xaa
1               5                   10                  15

Xaa Xaa Xaa

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 12

Phe Arg Cys Leu Val Glu Asn Arg Gly Asp Val Pro Phe Val Arg His
1               5                   10                  15

<210> SEQ ID NO 13
<211> LENGTH: 19
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: AMIDATION

<400> SEQUENCE: 13

Phe Arg Cys Leu Val Glu Asn Arg Gly Asp Val Pro Phe Val Lys Arg
1               5                   10                  15

Glu Arg Phe

<210> SEQ ID NO 14
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 14

Tyr Ser Gly Ala Phe Arg Leu Leu Ala Glu Gly Arg Gly Asp Val Ala
1               5                   10                  15

Phe Val Lys His Lys Lys
            20

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 15

Phe Arg Cys Leu Val Glu Asn Arg Gly Asp Val Pro Phe Val Thr Arg
1               5                   10                  15

Ile Arg

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Phe Arg Cys Leu Val Glu Asn Ala Gly Asp Val Ala Phe Val Arg His
1               5                   10                  15

<210> SEQ ID NO 17
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Tyr Ser Gly Ala Phe Arg Cys Leu Ala Glu Gly Ala Gly Asp Val Ala
1               5                   10                  15

Phe Val Lys His
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Tyr Arg Gly Ala Phe Arg Cys Leu Val Glu Asn Ala Gly Asp Val Ala
1               5                   10                  15

Phe Val Arg His
            20

<210> SEQ ID NO 19
<211> LENGTH: 19
<212> TYPE: PRT
<213> ORGANISM: Artificial Sequence
<220> FEATURE:
<223> OTHER INFORMATION: Synthetic peptide

<400> SEQUENCE: 19

Phe Arg Cys Leu Val Glu Asn Ala Gly Asp Val Ala Phe Val Arg His
1               5                   10                  15

Lys Lys Lys

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide

<400> SEQUENCE: 20

Phe Arg Cys Leu Val Glu Asn Ala Gly Asp Val Gly Phe Val Arg His
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

Phe Arg Cys Leu Val Glu Asn Ala Gly Asp Val Pro Phe Val Arg His
1               5                   10                  15

<210> SEQ ID NO 22
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 22

Phe Arg Cys Leu Val Glu Gln Ala Pro Asp Val Lys Phe Val Arg His
1               5                   10                  15

Lys Lys Lys

<210> SEQ ID NO 23
<211> LENGTH: 23
<212> TYPE: PRT
<213> ORGANISM: Artificial Sequence
<220> FEATURE:
<223> OTHER INFORMATION: Synthetic peptide

<400> SEQUENCE: 23

Tyr Ser Gly Ala Phe Arg Met Leu Ala Glu Gly Ala Gly Asp Val Ala
1               5                   10                  15

Phe Val Lys His Lys Lys Lys
            20

<210> SEQ ID NO 24
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (21)..(39)
<223> OTHER INFORMATION: Residues 21 to 39 are C to N-terminal

<400> SEQUENCE: 24

Phe Arg Cys Leu Val Glu Asn Ala Gly Asp Val Ala Phe Val Arg His
1               5                   10                  15

Lys Lys Lys Lys Lys Lys Lys His Arg Val Phe Ala Val Asp Gly Ala
            20                  25                  30

Asn Glu Val Leu Cys Arg Phe
        35

<210> SEQ ID NO 25
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is D-Phe
<220> FEATURE:
<221> NAME/KEY: MISC_FEATURE
<222> LOCATION: (2)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Cys
<220> FEATURE:
<221> NAME/KEY: MISC_FEATURE
<222> LOCATION: (4)..(4)
<223> OTHER INFORMATION: Xaa is D-Leu
<220> FEATURE:
<221> NAME/KEY: MISC_FEATURE
<222> LOCATION: (5)..(5)
<223> OTHER INFORMATION: Xaa is D-Val
<220> FEATURE:
<221> NAME/KEY: MISC_FEATURE
<222> LOCATION: (6)..(6)
<223> OTHER INFORMATION: Xaa is D-Glu
<220> FEATURE:
<221> NAME/KEY: MISC_FEATURE
```

```
<222> LOCATION: (7)..(7)
<223> OTHER INFORMATION: Xaa is D-Asn
<220> FEATURE:
<221> NAME/KEY: MISC_FEATURE
<222> LOCATION: (8)..(8)
<223> OTHER INFORMATION: Xaa is D-Ala
<220> FEATURE:
<221> NAME/KEY: MISC_FEATURE
<222> LOCATION: (10)..(10)
<223> OTHER INFORMATION: Xaa is D-Asp
<220> FEATURE:
<221> NAME/KEY: MISC_FEATURE
<222> LOCATION: (11)..(11)
<223> OTHER INFORMATION: Xaa is D-Val
<220> FEATURE:
<221> NAME/KEY: MISC_FEATURE
<222> LOCATION: (12)..(12)
<223> OTHER INFORMATION: Xaa is D-Ala
<220> FEATURE:
<221> NAME/KEY: MISC_FEATURE
<222> LOCATION: (13)..(13)
<223> OTHER INFORMATION: Xaa is D-Phe
<220> FEATURE:
<221> NAME/KEY: MISC_FEATURE
<222> LOCATION: (14)..(14)
<223> OTHER INFORMATION: Xaa is D-Val
<220> FEATURE:
<221> NAME/KEY: MISC_FEATURE
<222> LOCATION: (15)..(15)
<223> OTHER INFORMATION: Xaa is D-Arg
<220> FEATURE:
<221> NAME/KEY: MISC_FEATURE
<222> LOCATION: (16)..(16)
<223> OTHER INFORMATION: Xaa is D-His
<220> FEATURE:
<221> NAME/KEY: MISC_FEATURE
<222> LOCATION: (17)..(19)
<223> OTHER INFORMATION: Xaa is D-Lys

<400> SEQUENCE: 25

Xaa Xaa Xaa Xaa Xaa Xaa Xaa Xaa Gly Xaa Xaa Xaa Xaa Xaa Xaa
1               5                   10                  15

Xaa Xaa Xaa

<210> SEQ ID NO 26
<211> LENGTH: 16
<212> TYPE: PRT
<213> ORGANISM: Artificial Sequence
<220> FEATURE:
<223> OTHER INFORMATION: Synthetic peptide

<400> SEQUENCE: 26

Phe Arg Cys Leu Val Glu Asn Arg Gly Asp Val Pro Phe Val Arg His
1               5                   10                  15

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Phe Arg Cys Leu Val Glu Asn Arg Gly Asp Val Pro Phe Val Lys Arg
1               5                   10                  15

Glu Arg Phe

<210> SEQ ID NO 28
<211> LENGTH: 22
<212> TYPE: PRT
<213> ORGANISM: Artificial Sequence
```

-continued

```
<220> FEATURE:
<223> OTHER INFORMATION: Synthetic peptide

<400> SEQUENCE: 28

Tyr Ser Gly Ala Phe Arg Leu Leu Ala Glu Gly Arg Gly Asp Val Ala
1               5                   10                  15
Phe Val Lys His Lys Lys
            20

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide

<400> SEQUENCE: 29

Phe Arg Cys Leu Val Glu Asn Arg Gly Asp Val Pro Phe Val Thr Arg
1               5                   10                  15
Ile Arg

<210> SEQ ID NO 30
<211> LENGTH: 3963
<212> TYPE: DNA
<213> ORGANISM: Homo sapiens
<220> FEATURE:
<221> NAME/KEY: CDS
<222> LOCATION: (115)..(2331)

<400> SEQUENCE: 30
```

| | |
|---|---:|
| cacttaagga gctcgggcca gcgcgagggg gagcagggag gaagcccggc tgctgcggac | 60 |
| ctcctcggac ccggacccag ccccagcccg gccccagcca gccccgacgg cgcc atg<br>                                                                                                      Met<br>                                                                                                        1 | 117 |
| cgg ggt ccg agc ggg gct ctg tgg ctg ctc ctg gct ctg cgc acc gtg<br>Arg Gly Pro Ser Gly Ala Leu Trp Leu Leu Leu Ala Leu Arg Thr Val<br>              5                        10                      15 | 165 |
| ctc ggt ggc atg gag gtg cgg tgg tgc gcc acc tcg gac cca gag cag<br>Leu Gly Gly Met Glu Val Arg Trp Cys Ala Thr Ser Asp Pro Glu Gln<br>        20                      25                      30 | 213 |
| cac aag tgc ggc aac atg agc gag gcc ttc cgg gaa gcg ggc atc cag<br>His Lys Cys Gly Asn Met Ser Glu Ala Phe Arg Glu Ala Gly Ile Gln<br>  35                      40                      45 | 261 |
| ccc tcc ctc ctc tgc gtc cgg ggc acc tcc gcc gac cac tgc gtc cag<br>Pro Ser Leu Leu Cys Val Arg Gly Thr Ser Ala Asp His Cys Val Gln<br>50                      55                      60                      65 | 309 |
| ctc atc gcg gcc cag gag gct gac gcc atc act ctg gat gga gga gcc<br>Leu Ile Ala Ala Gln Glu Ala Asp Ala Ile Thr Leu Asp Gly Gly Ala<br>                  70                      75                      80 | 357 |
| atc tat gag gcg gga aag gag cac ggc ctg aag ccg gtg gtg ggc gaa<br>Ile Tyr Glu Ala Gly Lys Glu His Gly Leu Lys Pro Val Val Gly Glu<br>                      85                      90                      95 | 405 |
| gtg tac gat caa gag gtc ggt acc tcc tat tac gcc gtg gct gtg gtc<br>Val Tyr Asp Gln Glu Val Gly Thr Ser Tyr Tyr Ala Val Ala Val Val<br>                  100                     105                     110 | 453 |
| agg agg agc tcc cat gtg acc att gac acc ctg aaa ggc gtg aag tcc<br>Arg Arg Ser Ser His Val Thr Ile Asp Thr Leu Lys Gly Val Lys Ser<br>              115                     120                     125 | 501 |
| tgc cac acg ggc atc aat cgc aca gtg ggc tgg aac gtg ccc gtg ggc<br>Cys His Thr Gly Ile Asn Arg Thr Val Gly Trp Asn Val Pro Val Gly<br>130                      135                     140                     145 | 549 |

-continued

| | | |
|---|---|---|
| tac ctg gtg gag agc ggc cgc ctc tcg gtg atg ggc tgc gat gta ctc<br>Tyr Leu Val Glu Ser Gly Arg Leu Ser Val Met Gly Cys Asp Val Leu<br>150 155 160 | 597 | |
| aaa gct gtc agc gac tat ttt ggg ggc agc tgc gtc ccg ggg gca gga<br>Lys Ala Val Ser Asp Tyr Phe Gly Gly Ser Cys Val Pro Gly Ala Gly<br>165 170 175 | 645 | |
| gag acc agt tac tct gag tcc ctc tgt cgc ctc tgc agg ggt gac agc<br>Glu Thr Ser Tyr Ser Glu Ser Leu Cys Arg Leu Cys Arg Gly Asp Ser<br>180 185 190 | 693 | |
| tct ggg gaa ggg gtg tgt gac aag agc ccc ctg gag aga tac tac gac<br>Ser Gly Glu Gly Val Cys Asp Lys Ser Pro Leu Glu Arg Tyr Tyr Asp<br>195 200 205 | 741 | |
| tac agc ggg gcc ttc cgg tgc ctg gcg gaa ggg gca ggg gac gtg gct<br>Tyr Ser Gly Ala Phe Arg Cys Leu Ala Glu Gly Ala Gly Asp Val Ala<br>210 215 220 225 | 789 | |
| ttt gtg aag cac agc acg gta ctg gag aac acg gat ggg aag acg ctt<br>Phe Val Lys His Ser Thr Val Leu Glu Asn Thr Asp Gly Lys Thr Leu<br>230 235 240 | 837 | |
| ccc tcc tgg ggc cag gcc ctg ctg tca cag gac ttc gag ctg ctg tgc<br>Pro Ser Trp Gly Gln Ala Leu Leu Ser Gln Asp Phe Glu Leu Leu Cys<br>245 250 255 | 885 | |
| cgg gat ggt agc cgg gcc gat gtc acc gag tgg agg cag tgc cat ctg<br>Arg Asp Gly Ser Arg Ala Asp Val Thr Glu Trp Arg Gln Cys His Leu<br>260 265 270 | 933 | |
| gcc cgg gtg cct gct cac gcc gtg gtg gtc cgg gcc gac aca gat ggg<br>Ala Arg Val Pro Ala His Ala Val Val Val Arg Ala Asp Thr Asp Gly<br>275 280 285 | 981 | |
| ggc ctc atc ttc cgg ctg ctc aac gaa ggc cag cgt ctg ttc agc cac<br>Gly Leu Ile Phe Arg Leu Leu Asn Glu Gly Gln Arg Leu Phe Ser His<br>290 295 300 305 | 1029 | |
| gag ggc agc agc ttc cag atg ttc agc tct gag gcc tat ggc cag aag<br>Glu Gly Ser Ser Phe Gln Met Phe Ser Ser Glu Ala Tyr Gly Gln Lys<br>310 315 320 | 1077 | |
| gat cta ctc ttc aaa gac tct acc tcg gag ctt gtg ccc atc gcc aca<br>Asp Leu Leu Phe Lys Asp Ser Thr Ser Glu Leu Val Pro Ile Ala Thr<br>325 330 335 | 1125 | |
| cag acc tat gag gcg tgg ctg ggc cat gag tac ctg cac gcc atg aag<br>Gln Thr Tyr Glu Ala Trp Leu Gly His Glu Tyr Leu His Ala Met Lys<br>340 345 350 | 1173 | |
| ggt ctg ctc tgt gac ccc aac cgg ctg ccc ccc tac ctg cgc tgg tgt<br>Gly Leu Leu Cys Asp Pro Asn Arg Leu Pro Pro Tyr Leu Arg Trp Cys<br>355 360 365 | 1221 | |
| gtg ctc tcc act ccc gag atc cag aag tgt gga gac atg gcc gtg gcc<br>Val Leu Ser Thr Pro Glu Ile Gln Lys Cys Gly Asp Met Ala Val Ala<br>370 375 380 385 | 1269 | |
| ttc cgc cgg cag cgg ctc aag cca gag atc cag tgc gtg tca gcc aag<br>Phe Arg Arg Gln Arg Leu Lys Pro Glu Ile Gln Cys Val Ser Ala Lys<br>390 395 400 | 1317 | |
| tcc ccc caa cac tgc atg gag cgg atc cag gct gag cag gtc gac gct<br>Ser Pro Gln His Cys Met Glu Arg Ile Gln Ala Glu Gln Val Asp Ala<br>405 410 415 | 1365 | |
| gtg acc ctg agt ggc gag gac att tac acg gcg ggg aag acg tac ggc<br>Val Thr Leu Ser Gly Glu Asp Ile Tyr Thr Ala Gly Lys Thr Tyr Gly<br>420 425 430 | 1413 | |
| ctg gtt ccc gca gcc ggg gag cac tat gcc ccg gaa gac agc agc aac<br>Leu Val Pro Ala Ala Gly Glu His Tyr Ala Pro Glu Asp Ser Ser Asn<br>435 440 445 | 1461 | |
| tcg tac tac gtg gtg gcc gtg gtg aga cgg gac agc tcc cac gcc ttc<br>Ser Tyr Tyr Val Val Ala Val Val Arg Arg Asp Ser Ser His Ala Phe<br>450 455 460 465 | 1509 | |

```
acc ttg gat gag ctt cgg ggc aag cgc tcc tgc cac gcc ggt ttc ggc      1557
Thr Leu Asp Glu Leu Arg Gly Lys Arg Ser Cys His Ala Gly Phe Gly
                470                 475                 480 agc cct gca ggc tgg gat gtc ccc gtg ggt gcc ctt att cag aga ggc      1605
Ser Pro Ala Gly Trp Asp Val Pro Val Gly Ala Leu Ile Gln Arg Gly
            485                 490                 495 ttc atc cgg ccc aag gac tgt gac gtc ctc aca gca gtg agc gag ttc      1653
Phe Ile Arg Pro Lys Asp Cys Asp Val Leu Thr Ala Val Ser Glu Phe
        500                 505                 510 ttc aat gcc agc tgc gtg ccc gtg aac aac ccc aag aac tac ccc tcc      1701
Phe Asn Ala Ser Cys Val Pro Val Asn Asn Pro Lys Asn Tyr Pro Ser
    515                 520                 525 tcg ctg tgt gca ctg tgc gtg ggg gac gag cag ggc cgc aac aag tgt      1749
Ser Leu Cys Ala Leu Cys Val Gly Asp Glu Gln Gly Arg Asn Lys Cys
530                 535                 540                 545 gtg ggc aac agc cag gag cgg tat tac ggc tac cgc ggc gcc ttc agg      1797
Val Gly Asn Ser Gln Glu Arg Tyr Tyr Gly Tyr Arg Gly Ala Phe Arg
                550                 555                 560 tgc ctg gtg gag aat gcg ggt gac gtt gcc ttc gtc agg cac aca acc      1845
Cys Leu Val Glu Asn Ala Gly Asp Val Ala Phe Val Arg His Thr Thr
            565                 570                 575 gtc ttt gac aac aca aac ggc cac aat tcc gag ccc tgg gct gct gag      1893
Val Phe Asp Asn Thr Asn Gly His Asn Ser Glu Pro Trp Ala Ala Glu
        580                 585                 590 ctc agg tca gag gac tat gaa ctg ctg tgc ccc aac ggg gcc cga gcc      1941
Leu Arg Ser Glu Asp Tyr Glu Leu Leu Cys Pro Asn Gly Ala Arg Ala
    595                 600                 605 gag gtg tcc cag ttt gca gcc tgc aac ctg gca cag ata cca ccc cac      1989
Glu Val Ser Gln Phe Ala Ala Cys Asn Leu Ala Gln Ile Pro Pro His
610                 615                 620                 625 gcc gtg atg gtc cgg ccc gac acc aac atc ttc acc gtg tat gga ctg      2037
Ala Val Met Val Arg Pro Asp Thr Asn Ile Phe Thr Val Tyr Gly Leu
                630                 635                 640 ctg gac aag gcc cag gac ctg ttt gga gac gac cac aat aag aac ggg      2085
Leu Asp Lys Ala Gln Asp Leu Phe Gly Asp Asp His Asn Lys Asn Gly
            645                 650                 655 ttc aaa atg ttc gac tcc tcc aac tat cat ggc caa gac ctg ctt ttc      2133
Phe Lys Met Phe Asp Ser Ser Asn Tyr His Gly Gln Asp Leu Leu Phe
        660                 665                 670 aag gat gcc acc gtc cgg gcg gtg cct gtc gga gag aaa acc acc tac      2181
Lys Asp Ala Thr Val Arg Ala Val Pro Val Gly Glu Lys Thr Thr Tyr
    675                 680                 685 cgc ggc tgg ctg ggg ctg gac tac gtg gcg gcg ctg gaa ggg atg tcg      2229
Arg Gly Trp Leu Gly Leu Asp Tyr Val Ala Ala Leu Glu Gly Met Ser
690                 695                 700                 705 tct cag cag tgc tcg ggc gca gcg gcc ccg gcg ccc ggg gcg ccc ctg      2277
Ser Gln Gln Cys Ser Gly Ala Ala Ala Pro Ala Pro Gly Ala Pro Leu
                710                 715                 720 ctc ccg ctg ctg ctg ccc gcc ctc gcc gcc cgc ctg ctc ccg ccc gcc      2325
Leu Pro Leu Leu Leu Pro Ala Leu Ala Ala Arg Leu Leu Pro Pro Ala
            725                 730                 735 ctc tga gcccggccgc cccgccccag agctccgatg cccgcccggg gagtttccgc       2381
Leu ggcggcttcg cgctggaatc cagaaggaag ctcgcgaagg ccgggcccgg cgtgggcggg    2441
agcaggcgcc tccccgggag ccccgccgcc cacgggcgcc acctggcgct gctacctgag    2501
gcgccgcccc cgggccgcg cggccttcc cgccaaccgc cgcctcccgc cacctggagc      2561
cgcgcgggcc gcgccggagg aggccggttg cccaggaaac cgctgagtcc gggcttcccg    2621
```

```
ccgcccgccc cgcggtgtcg cccgagggc cgcccgcct cctccccgca gccccgcgcc    2681
cccgtccgcg aggcccctg gggacgcggt ggccgccgag gcgcctacac ccgcaggccg    2741
cggccaggcc gtcccaggag gccccggcgc aacgggacc cggcgcgtgg acagcggcc     2801
tctgctggcg gcggcgggag ggaggccgga ccggggcgac ggggagaagc cttcgcccgc   2861
gggaccgtgt ccggggtggg ggctccagtt cctccgaccg cccgtgcgct gggagggagg   2921
ccgagcccgg ggaacgccgc gtgccctgcc tcgtccccca ctgtggccgc gccagctcca   2981
tcccgggcca gccgcgtcca cgggccccct cccgagtctc ctcaggctct cgcctcccct   3041
accccgtgg gatgcccacc gcccgcaccc acgcccgagc ctggcggcag cagccgcccc   3101
ccgcctgaag ggagccggag gtgacccagg ccgcgggctc ccgaggcccc tgaagggctg   3161
cgcgtgggga cccgccatgc ttctgggttc cgaacggggg tgagctccgt ctcctcaccc   3221
ggccccgcac ccgctgggcc tggggacccc tcactccccg tgcccgcccc tccgcgaggc   3281
agcagaaagc gcccggccgg ggcctctctc tactccatct tgccacagtt gtctgagaag   3341
ccagaaaaag tttccagaac tggcagccct taaaaaaaat gaagaggaag agaagaaatg   3401
ggagcaggca gccctcgtca gcagaccggg agccgcgtgg gcgcggagcc atttgcattc   3461
cggtctgcgg gggctcgggg atgctggtga caggcccggt tcccggtggc tcgcccccac   3521
ctgcgggcgt cgggaaggat cccttccatc tctcagccgc agaggaggcc ctggcagcgc   3581
cccggctgta gccatgcaac cccgaggagt cccgggcacc ttcaccccac cgggaggggc   3641
cacaaggacc tgggcctcgg ccaccaagct ttgtcccctc tcgctgtggg gggctagtga   3701
ttctcctccg acctgacgat tgcttggttt tttcaaaagg gagttttgtg cggtgagaag   3761
tgtgtttctg tgtggctaac tctgggctag cgtgccgtgg ccattgaagg tgtggcctgc   3821
gtgggtgcag tgtaagtgac gctggattgt caggtggcag caggggaccc ctgctgtgtc   3881
agtgctaatg aaacatgttg gttggtttct aaaataaagc caaacaagcc agcacatgca   3941
gaggcttgga ccctgataga aa                                            3963
```

<210> SEQ ID NO 31
<211> LENGTH: 738
<212> TYPE: PRT
<213> ORGANISM: Homo sapiens

<400> SEQUENCE: 31

Met Arg Gly Pro Ser Gly Ala Leu Trp Leu Leu Ala Leu Arg Thr
1               5                   10                  15

Val Leu Gly Gly Met Glu Val Arg Trp Cys Ala Thr Ser Asp Pro Glu
                20                  25                  30

Gln His Lys Cys Gly Asn Met Ser Glu Ala Phe Arg Glu Ala Gly Ile
            35                  40                  45

Gln Pro Ser Leu Leu Cys Val Arg Gly Thr Ser Ala Asp His Cys Val
        50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
            100                 105                 110

Val Arg Arg Ser Ser His Val Thr Ile Asp Thr Leu Lys Gly Val Lys
        115                 120                 125

-continued

```
Ser Cys His Thr Gly Ile Asn Arg Thr Val Gly Trp Asn Val Pro Val
130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Ser Cys Val Pro Gly Ala
                165                 170                 175

Gly Glu Thr Ser Tyr Ser Glu Ser Leu Cys Arg Leu Cys Arg Gly Asp
                180                 185                 190

Ser Ser Gly Glu Gly Val Cys Asp Lys Ser Pro Leu Glu Arg Tyr Tyr
            195                 200                 205

Asp Tyr Ser Gly Ala Phe Arg Cys Leu Ala Glu Gly Ala Gly Asp Val
210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255

Cys Arg Asp Gly Ser Arg Ala Asp Val Thr Glu Trp Arg Gln Cys His
                260                 265                 270

Leu Ala Arg Val Pro Ala His Ala Val Val Arg Ala Asp Thr Asp
            275                 280                 285

Gly Gly Leu Ile Phe Arg Leu Leu Asn Glu Gly Gln Arg Leu Phe Ser
290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
            340                 345                 350

Lys Gly Leu Leu Cys Asp Pro Asn Arg Leu Pro Pro Tyr Leu Arg Trp
            355                 360                 365

Cys Val Leu Ser Thr Pro Glu Ile Gln Lys Cys Gly Asp Met Ala Val
370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
            420                 425                 430

Gly Leu Val Pro Ala Ala Gly Glu His Tyr Ala Pro Glu Asp Ser Ser
            435                 440                 445

Asn Ser Tyr Tyr Val Val Ala Val Val Arg Arg Asp Ser Ser His Ala
450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510

Phe Phe Asn Ala Ser Cys Val Pro Val Asn Asn Pro Lys Asn Tyr Pro
            515                 520                 525

Ser Ser Leu Cys Ala Leu Cys Val Gly Asp Glu Gln Gly Arg Asn Lys
530                 535                 540

Cys Val Gly Asn Ser Gln Glu Arg Tyr Tyr Gly Tyr Arg Gly Ala Phe
```

```
             545                 550                 555                 560
Arg Cys Leu Val Glu Asn Ala Gly Asp Val Ala Phe Val Arg His Thr
                    565                 570                 575

Thr Val Phe Asp Asn Thr Asn Gly His Asn Ser Glu Pro Trp Ala Ala
                580                 585                 590

Glu Leu Arg Ser Glu Asp Tyr Glu Leu Leu Cys Pro Asn Gly Ala Arg
            595                 600                 605

Ala Glu Val Ser Gln Phe Ala Ala Cys Asn Leu Ala Gln Ile Pro Pro
        610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp His Asn Lys Asn
                    645                 650                 655

Gly Phe Lys Met Phe Asp Ser Ser Asn Tyr His Gly Gln Asp Leu Leu
                660                 665                 670

Phe Lys Asp Ala Thr Val Arg Ala Val Pro Val Gly Glu Lys Thr Thr
            675                 680                 685

Tyr Arg Gly Trp Leu Gly Leu Asp Tyr Val Ala Ala Leu Glu Gly Met
        690                 695                 700

Ser Ser Gln Gln Cys Ser Gly Ala Ala Ala Pro Ala Pro Gly Ala Pro
705                 710                 715                 720

Leu Leu Pro Leu Leu Pro Ala Leu Ala Ala Arg Leu Leu Pro Pro
                    725                 730                 735

Ala Leu

<210> SEQ ID NO 32
<211> LENGTH: 332
<212> TYPE: PRT
<213> ORGANISM: Homo sapiens

<400> SEQUENCE: 32

Arg Trp Cys Ala Thr Ser Asp Pro Glu Gln His Lys Cys Gly Asn Met
1               5                   10                  15

Ser Glu Ala Phe Arg Glu Ala Gly Ile Gln Pro Ser Leu Leu Cys Val
                20                  25                  30

Arg Gly Thr Ser Ala Asp His Cys Val Gln Leu Ile Ala Ala Gln Glu
            35                  40                  45

Ala Asp Ala Ile Thr Leu Asp Gly Gly Ala Ile Tyr Glu Ala Gly Lys
        50                  55                  60

Glu His Gly Leu Lys Pro Val Val Gly Glu Val Tyr Asp Gln Glu Val
65                  70                  75                  80

Gly Thr Ser Tyr Tyr Ala Val Ala Val Val Arg Arg Ser Ser His Val
                85                  90                  95

Thr Ile Asp Thr Leu Lys Gly Val Lys Ser Cys His Thr Gly Ile Asn
            100                 105                 110

Arg Thr Val Gly Trp Asn Val Pro Val Gly Tyr Leu Val Glu Ser Gly
        115                 120                 125

Arg Leu Ser Val Met Gly Cys Asp Val Leu Lys Ala Val Ser Asp Tyr
    130                 135                 140

Phe Gly Gly Ser Cys Val Pro Gly Ala Gly Glu Thr Ser Tyr Ser Glu
145                 150                 155                 160

Ser Leu Cys Arg Leu Cys Arg Gly Asp Ser Ser Gly Glu Gly Val Cys
                165                 170                 175

Asp Lys Ser Pro Leu Glu Arg Tyr Tyr Asp Tyr Ser Gly Ala Phe Arg
```

```
                    180                 185                 190
Cys Leu Ala Glu Gly Ala Gly Asp Val Ala Phe Val Lys His Ser Thr
            195                 200                 205
Val Leu Glu Asn Thr Asp Gly Lys Thr Leu Pro Ser Trp Gly Gln Ala
        210                 215                 220
Leu Leu Ser Gln Asp Phe Glu Leu Leu Cys Arg Asp Gly Ser Arg Ala
225                 230                 235                 240
Asp Val Thr Glu Trp Arg Gln Cys His Leu Ala Arg Val Pro Ala His
                245                 250                 255
Ala Val Val Val Arg Ala Asp Thr Asp Gly Gly Leu Ile Phe Arg Leu
            260                 265                 270
Leu Asn Glu Gly Gln Arg Leu Phe Ser His Glu Gly Ser Ser Phe Gln
        275                 280                 285
Met Phe Ser Ser Glu Ala Tyr Gly Gln Lys Asp Leu Leu Phe Lys Asp
    290                 295                 300
Ser Thr Ser Glu Leu Val Pro Ile Ala Thr Gln Thr Tyr Glu Ala Trp
305                 310                 315                 320
Leu Gly His Glu Tyr Leu His Ala Met Lys Gly Leu
                325                 330

<210> SEQ ID NO 33
<211> LENGTH: 338
<212> TYPE: PRT
<213> ORGANISM: Homo sapiens

<400> SEQUENCE: 33

Arg Trp Cys Val Leu Ser Thr Pro Glu Ile Gln Lys Cys Gly Asp Met
1               5                   10                  15
Ala Val Ala Phe Arg Arg Gln Arg Leu Lys Pro Glu Ile Gln Cys Val
            20                  25                  30
Ser Ala Lys Ser Pro Gln His Cys Met Glu Arg Ile Gln Ala Glu Gln
        35                  40                  45
Val Asp Ala Val Thr Leu Ser Gly Glu Asp Ile Tyr Thr Ala Gly Lys
    50                  55                  60
Thr Tyr Gly Leu Val Pro Ala Ala Gly Glu His Tyr Ala Pro Glu Asp
65                  70                  75                  80
Ser Ser Asn Ser Tyr Tyr Val Val Ala Val Arg Arg Asp Ser Ser
                85                  90                  95
His Ala Phe Thr Leu Asp Glu Leu Arg Gly Lys Arg Ser Cys His Ala
            100                 105                 110
Gly Phe Gly Ser Pro Ala Gly Trp Asp Val Pro Val Gly Ala Leu Ile
        115                 120                 125
Gln Arg Gly Phe Ile Arg Pro Lys Asp Cys Asp Val Leu Thr Ala Val
    130                 135                 140
Ser Glu Phe Phe Asn Ala Ser Cys Val Pro Val Asn Asn Pro Lys Asn
145                 150                 155                 160
Tyr Pro Ser Ser Leu Cys Ala Leu Cys Val Gly Asp Glu Gln Gly Arg
                165                 170                 175
Asn Lys Cys Val Gly Asn Ser Gln Glu Arg Tyr Tyr Gly Tyr Arg Gly
            180                 185                 190
Ala Phe Arg Cys Leu Val Glu Asn Ala Gly Asp Val Ala Phe Val Arg
        195                 200                 205
His Thr Thr Val Phe Asp Asn Thr Asn Gly His Asn Ser Glu Pro Trp
    210                 215                 220
```

-continued

```
Ala Ala Glu Leu Arg Ser Glu Asp Tyr Glu Leu Leu Cys Pro Asn Gly
225                 230                 235                 240

Ala Arg Ala Glu Val Ser Gln Phe Ala Ala Cys Asn Leu Ala Gln Ile
                245                 250                 255

Pro Pro His Ala Val Met Val Arg Pro Asp Thr Asn Ile Phe Thr Val
            260                 265                 270

Tyr Gly Leu Leu Asp Lys Ala Gln Asp Leu Phe Gly Asp Asp His Asn
            275                 280                 285

Lys Asn Gly Phe Lys Met Phe Asp Ser Ser Asn Tyr His Gly Gln Asp
            290                 295                 300

Leu Leu Phe Lys Asp Ala Thr Val Arg Ala Val Pro Val Gly Glu Lys
305                 310                 315                 320

Thr Thr Tyr Arg Gly Trp Leu Gly Leu Asp Tyr Val Ala Ala Leu Glu
                325                 330                 335

Gly Met
```

PEPTIDE COMPOUNDS DERIVED FROM MELANOTRANSFERRIN AND USES THEREOF

CROSS-REFERENCE TO RELATED APPLICATIONS

This application is a National Entry Application of PCT application no. PCT/CA2012/050741 filed on Oct. 18, 2012 and published in English under PCT Article 21(2), which itself claims benefit of U.S. provisional application Ser. No. 61/548,905, filed on Oct. 19, 2011. All documents above are incorporated herein by reference in their entirety.

TECHNICAL FIELD

The present invention generally relates to the field of regulation of plasminogen activation, and more particularly to the field of modulation of angiogenesis and cell migration. More specifically, the invention concerns peptide compounds, compositions thereof, methods of preparation thereof, and uses thereof, such as for modulation of plasminogen activation, modulation of angionenesis and/or cell migration, and/or the treatment of angiogenesis-related disorders, such as cancer.

SEQUENCE LISTING

Pursuant to 37 C.F.R. 1.821(c), a sequence listing is submitted herewith as an ASCII compliant text file named "Sequence listing_ST25.txt", created on Oct. 16, 2012 and having a size of ~44 kilobytes. The content of the aforementioned file is hereby incorporated by reference in its entirety.

BACKGROUND ART

Angiogenesis, the growth of new blood vessels from the existing vasculature in the body, is involved in physiological and pathological processes such as embryonic development, wound healing, reproductive cycles, diabetic retinopathy, chronic inflammation, tumor growth and metastasis. This process involves endothelial cell (EC) proliferation, migration and morphogenic differentiation into capillary-like structures (tubulogenesis). Tumor angiogenesis is the proliferation of a network of blood vessels that penetrates into cancerous growths, supplying nutrients and oxygen and removing waste products. Tumor angiogenesis actually starts with tumor cells releasing molecules (known as angiogenic growth factors) that send signals to surrounding normal host tissue. This signaling activates certain genes in the host tissue that, in turn, make proteins to encourage growth of new blood vessels.

Metastasis is the process by which cancer spreads from the place at which it first arose as a primary tumor to distant locations in the body via the bloodstream or the lymphatic system. Active migration of tumour cells is thus a prerequisite for tumour-cell invasion and metastasis.

Thus, the inhibition or suppression of abnormal angiogenesis and cell migration may provide therapeutic strategies for the treatment of angiogenesis-dependent disorders.

There is a need to provide new therapeutics that can modulate angiogenesis and cell migration, and for the treatment of angiogenesis-related disorders such as cancer.

The present description refers to a number of documents, the content of which is herein incorporated by reference in their entirety.

SUMMARY OF THE INVENTION

The present invention relates to peptide compounds, compositions thereof, methods of preparation thereof, and uses thereof, such as for modulation of plasminogen activation, modulation of angionenesis and/or cell migration, and/or the treatment of angiogenesis-related disorders, such as cancer.

In a first aspect, the present invention provides a peptide compound that increases plasminogen activation by urokinase-type plasminogen activator (uPA), said peptide compound comprising a domain comprising a sequence derived from residues 210-229 or 556-575 of the polypeptide of SEQ ID NO:1.

In an embodiment, the above-mentioned domain is a domain of formula I:

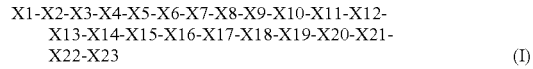
X13-X14-X15-X16-X17-X18-X19-X20-X21-
X22-X23      (I)

wherein
"-" is a bond;
X1 is an aromatic residue or is absent; X2 is a basic residue, Ser, D-Ser or is absent; X3 is Gly or is absent; X4 is Ala, D-Ala or is absent; X5 is an aromatic residue; X6 is a basic amino acid; X7 is Cys or D-Cys, Met, D-Met, Leu or D-Leu or Gly; X8 is Leu, or D-Leu; X9 is Val, D-Val, Ala or D-Ala; X10 is an acidic residue; X11 is Asn, D-Asn, Gln, D-Gln or Gly; X12 is a basic residue, Ala or D-Ala; X13 is Pro, D-Pro or Gly; X14 is an acidic residue; X15 is Val or D-Val; X16 is Ala, D-Ala, Pro, D-Pro, Lys, D-Lys or Gly; X17 is an aromatic residue; X18 is Val or D-Val; X19 is a basic residue, Thr or D-Thr; X20 is a basic residue; X21 is a basic residue, an acidic residue, Ile, D-Ile, or is absent; X22 is a basic residue or is absent; and X23 is a basic residue, an aromatic residue or is absent, or a salt thereof.

In a further aspect, the present invention provides a peptide compound comprising a domain of formula I:

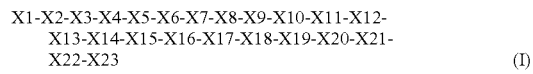
X13-X14-X15-X16-X17-X18-X19-X20-X21-
X22-X23      (I)

wherein
"-" is a bond;
X1 is an aromatic residue or is absent; X2 is a basic residue, Ser, D-Ser or is absent; X3 is Gly or is absent; X4 is Ala, D-Ala or is absent; X5 is an aromatic residue; X6 is a basic amino acid; X7 is Cys or D-Cys, Met, D-Met, Leu or D-Leuor Gly; X8 is Leu, or D-Leu; X9 is Val, D-Val, Ala or D-Ala; X10 is an acidic residue; X11 is Asn, D-Asn, Gln, D-Gln or Gly; X12 is a basic residue, Ala or D-Ala; X13 is Pro, D-Pro or Gly; X14 is an acidic residue; X15 is Val or D-Val; X16 is Ala, D-Ala, Pro, D-Pro, Lys, D-Lys or Gly; X17 is an aromatic residue; X18 is Val or D-Val; X19 is a basic residue, Thr or D-Thr; X20 is a basic residue; X21 is a basic residue, an acidic residue, Ile, D-Ile, or is absent; X22 is a basic residue or is absent; and X23 is a basic residue, an aromatic residue or is absent, or a salt thereof.

In embodiments, X1 is Tyr, D-Tyr or is absent; X2 is Arg, D-Arg, Ser, D-Ser or is absent; X4 is Ala or is absent; X5 is Phe or D-Phe; X6 is Arg or D-Arg; X7 is Cys, D-Cys, Met or D-Met; X10 is Glu or D-Glu; X11 is Asn, D-Asn or Gly; X12 is Arg, D-Arg, Ala or D-Ala; X13 is Gly; X14 is Asp or D-Asp; X17 is Phe or D-Phe; X19 is Arg, D-Arg, Lys, D-Lys, Thr or D-Thr; X20 is His, D-His, Arg or D-Arg; X21 is Lys, D-Lys, Glu, D-Glu, Ile, D-Ile, or is absent; X22 is Lys, D-Lys, Arg, D-Arg, or is absent; and/or X23 is Lys, D-Lys, Phe, D-Phe, or is absent.

In an embodiment, X1, X2, X3 and/or X4 is/are absent; in a further embodiment X1 to X4 are absent. In another embodiment, X21, X22 and/or X23 is/are absent; in a further embodiment X21 to X23 are absent.

In an embodiment, the above-mentioned domain is:

(a)
(SEQ ID NO: 16)
F-R-C-L-V-E-N-A-G-D-V-A-F-V-R-H;

(b)
(SEQ ID NO: 17)
Y-S-G-A-F-R-C-L-A-E-G-A-G-D-V-A-F-V-K-H;

(c)
(SEQ ID NO: 18)
Y-R-G-A-F-R-C-L-V-E-N-A-G-D-V-A-F-V-R-H;

(d)
(SEQ ID NO: 19)
F-R-C-L-V-E-N-A-G-D-V-A-F-V-R-H-K-K-K;

(e)
(SEQ ID NO: 20)
F-R-C-L-V-E-N-A-G-D-V-G-F-V-R-H;

(f)
(SEQ ID NO: 21)
F-R-C-L-V-E-N-A-G-D-V-P-F-V-R-H;

(g)
(SEQ ID NO: 22)
F-R-C-L-V-E-Q-A-P-D-V-K-F-V-R-H-K-K-K;

(h)
(SEQ ID NO: 23)
Y-S-G-A-F-R-M-L-A-E-G-A-G-D-V-A-F-V-K-H-K-K-K;

(i)
(SEQ ID NO: 24)
•F-R-C-L-V-E-N-A-G-D-V-A-F-V-R-H-K-K-K
•F-R-C-L-V-E-N-A-G-D-V-A-F-V-R-H-K-K-K⟩K;

(j)
(SEQ ID NO: 25)
f-r-c-l-v-e-n-a-G-d-v-a-f-v-r-h-k-k-k;

(k)
(SEQ ID NO: 26)
F-R-C-L-V-E-N-R-G-D-V-P-F-V-R-H;

(l)
(SEQ ID NO: 27)
F-R-C-L-V-E-N-R-G-D-V-P-F-V-K-R-E-R-F;

(m)
(SEQ ID NO: 28)
Y-S-G-A-F-R-L-L-A-E-G-R-G-D-V-A-F-V-K-H-K-K; or (n)
(SEQ ID NO: 29)
F-R-C-L-V-E-N-R-G-D-V-P-F-V-T-R-I-R;

wherein f=D-Phe, r=D-Arg, c=D-Cys, l=D-Leu, v=D-Val, e=D-Glu, n=D-Asn, a=D-Ala, d=D-Asp, h=D-His, and k=D-Lys, or a salt thereof.

In an embodiment, the above-mentioned peptide compound further comprises (i) an amino-terminal modifying group; (ii) a carboxy-terminal modifying group; or (iii) both (i) and (ii).

In a further embodiment, the above-mentioned amino-terminal modifying group is a linear or branched saturated $C_1$-$C_6$ acyl group or unsaturated $C_3$-$C_6$ acyl group. In a further embodiment, the above-mentioned amino-terminal modifying group is an acetyl group (Ac).

In another embodiment, the above-mentioned carboxy-terminal modifying group is $NH_2$.

In an embodiment, the above-mentioned peptide compound is:

(a)
(SEQ ID NO: 2)
Ac-F-R-C-L-V-E-N-A-G-D-V-A-F-V-R-H-NH$_2$;

(b)
(SEQ ID NO: 3)
Ac-Y-S-G-A-F-R-C-L-A-E-G-A-G-D-V-A-F-V-K-H-NH$_2$;

(c)
(SEQ ID NO: 4)
Ac-Y-R-G-A-F-R-C-L-V-E-N-A-G-D-V-A-F-V-R-H-NH$_2$;

(d)
(SEQ ID NO: 5)
Ac-F-R-C-L-V-E-N-A-G-D-V-A-F-V-R-H-K-K-K-NH$_2$;

(e)
(SEQ ID NO: 6)
Ac-F-R-C-L-V-E-N-A-G-D-V-G-F-V-R-H-NH$_2$;

(f)
(SEQ ID NO: 7)
Ac-F-R-C-L-V-E-N-A-G-D-V-P-F-V-R-H-NH$_2$;

(g)
(SEQ ID NO: 8)
Ac-F-R-C-L-V-E-Q-A-P-D-V-K-F-V-R-H-K-K-K-NH$_2$;

(h)
(SEQ ID NO: 9)
Ac-Y-S-G-A-F-R-M-L-A-E-G-A-G-D-V-A-F-V-K-H-K-K-K-NH$_2$;

(i)
(SEQ ID NO: 10)
Ac-F-R-C-L-V-E-N-A-G-D-V-A-F-V-R-H-K-K-K
Ac-F-R-C-L-V-E-N-A-G-D-V-A-F-V-R-H-K-K-K⟩K-NH$_2$;

(j)
(SEQ ID NO: 11)
Ac-f-r-c-l-v-e-n-a-G-d-v-a-f-v-r-h-k-k-k-NH$_2$;

(k)
(SEQ ID NO: 12)
Ac-F-R-C-L-V-E-N-R-G-D-V-P-F-V-R-H-NH$_2$;

(l)
(SEQ ID NO: 13)
Ac-F-R-C-L-V-E-N-R-G-D-V-P-F-V-K-R-E-R-F-NH$_2$;

(m)
(SEQ ID NO: 14)
Ac-Y-S-G-A-F-R-L-L-A-E-G-R-G-D-V-A-F-V-K-H-K-K-NH$_2$; or (n)
(SEQ ID NO: 15)
Ac-F-R-C-L-V-E-N-R-G-D-V-P-F-V-T-R-I-R-NH$_2$;

wherein Ac=acetyl, f=D-Phe, r=D-Arg, c=D-Cys, l=D-Leu, v=D-Val, e=D-Glu, n=D-Asn, a=D-Ala, d=D-Asp, h=D-His, and k=D-Lys, or a salt thereof.

In another embodiment, the above-mentioned bond is a peptide bond.

In another aspect, the present invention provides a pharmaceutical composition comprising the above-mentioned peptide compound. In an embodiment, the above-mentioned pharmaceutical composition further comprises one or more pharmaceutically acceptable carriers, excipient, and/or diluents.

In another aspect, the present invention provides a method of inhibiting angiogenesis and/or cell migration in a subject comprising administering an effective amount of the above-mentioned peptide compound, or the above-mentioned pharmaceutical composition, to a subject in need thereof.

In another aspect, the present invention provides a method of treating cancer comprising administering an effective amount of the above-mentioned peptide compound, or the above-mentioned pharmaceutical composition, to a subject in need thereof.

In another aspect, the present invention provides the use of the above-mentioned peptide compound, or the above-mentioned pharmaceutical composition for inhibiting angiogenesis and/or cell migration in a subject.

In another aspect, the present invention provides the use of the above-mentioned peptide compound, or the above-mentioned pharmaceutical composition, for the manufacture of a medicament for inhibiting angiogenesis and/or cell migration in a subject.

In another aspect, the present invention provides the use of the above-mentioned peptide compound, or the above-mentioned pharmaceutical composition for treating cancer in a subject.

In another aspect, the present invention provides the use of the above-mentioned peptide compound, or the above-mentioned pharmaceutical composition for the manufacture of a medicament for treating cancer in a subject.

In another aspect, the present invention provides the above-mentioned peptide compound, or the above-mentioned pharmaceutical composition, for use as a medicament. In an embodiment, the above-mentioned medicament is for inhibiting angiogenesis and/or cell migration in a subject. In another embodiment, the above-mentioned medicament is for treating cancer in a subject.

In another aspect, the present invention provides the above-mentioned peptide compound, or the above-mentioned pharmaceutical composition, for inhibiting angiogenesis and/or cell migration in a subject.

In another aspect, the present invention provides the above-mentioned peptide compound, or the above-mentioned pharmaceutical composition, for treating cancer in a subject.

In another aspect, the present invention provides the above-mentioned peptide compound, or the above-mentioned pharmaceutical composition, for use in a method for inhibiting angiogenesis and/or cell migration in a subject.

In another aspect, the present invention provides the above-mentioned peptide compound, or the above-mentioned pharmaceutical composition, for use in a method for treating cancer in a subject.

In another aspect, the present invention provides the above-mentioned peptide compound, or the above-mentioned pharmaceutical composition, for the manufacture of a medicament for inhibiting angiogenesis and/or cell migration in a subject.

In another aspect, the present invention provides the above-mentioned peptide compound, or the above-mentioned pharmaceutical composition, for the manufacture of a medicament for treating cancer in a subject.

In an embodiment, the above-mentioned cancer is melanoma, prostate cancer, leukemia, hormone dependent cancer, breast cancer, colon cancer, lung cancer, skin cancer, ovarian cancer, pancreatic cancer, bone cancer, liver cancer, biliary cancer, lymphoma, sarcoma, esophageal cancer, stomach cancer, brain cancer, kidney cancer or epidermal cancer.

In an embodiment, the above-mentioned peptide compound is administered intravenously, orally, transdermally, subcutaneously, mucosally, intramuscularly, intranasally, intrapulmonary, parenterally, intrarectally or topically.

In an embodiment, the above-mentioned peptide compound or pharmaceutical composition is for intravenous, oral, transdermal, subcutaneous, mucosal, intramuscular, intranasal, intrapulmonary, parenteral, intrarectal or topical administration. In another embodiment, the above-mentioned pharmaceutical composition is adapted for intravenous, oral, transdermal, subcutaneous, mucosal, intramuscular, intranasal, intrapulmonary, parenteral, intrarectal or topical administration.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A: Screening of the sMTf-derived peptides for their ability to stimulate plasminogen activation by uPA. FIG. 1B: Plasminogen activation by uPA was measured in the presence or absence of various concentrations of peptide of SEQ ID NO: 2. uPA-dependent plasminogen activation was performed using a colorimetric assay as described in Example 1. Data represent the means±SD and the results are expressed as VLK-pNA hydrolysis velocity (mAU/min). Statistically significant differences, as compared to control conditions, are indicated by * $p \leq 0.05$,  $p \leq 0.01$, * $p \leq 0.001$;

FIG. 3A: Effect of peptide of SEQ ID NO: 10 on NCI-H460 growth. FIG. 3B: Effect of peptides of SEQ ID NOs: 5 and 7 on NCI-H460 growth. FIG. 3C: Effect of peptides of SEQ ID NOs: 9, 13 and 15 on NCI-H460 growth. Data represent the means±SE and the results are expressed as a tumor volume ($mm^3$). Control=vehicle only;

FIG. 4A: Effect of peptides of SEQ ID NOs: 5 and 7 on U87 growth. FIG. 4B: Effect of peptides SEQ ID NOs: 13 and 15 on U87 growth. Data represent the means±SE and the results are expressed as a tumor volume (mm$^3$). Control=vehicle only;

FIGS. 5A and 5B show the initial and final tumor volume (mm$^3$), as well as the deltaC/deltaT ($\Delta C/\Delta T$) values (%), for NCI-H460 lung carcinoma (FIG. 5A) and U87 glioblastoma tumor xenograft (FIG. 5B) experiments;

FIG. 6 shows an evaluation of the cellular toxicity effects of the sMTf-derived peptide of SEQ ID NO: 2. Cellular toxicity was evaluated using the [methyl-$^3$H]-thymidine incorporation as described in Example 1. The cellular toxicity was performed in the presence or absence of various concentrations of the sMTf-derived peptide of SEQ ID NO: 2 on HMEC-1 endothelial cells and NCI-H460 pulmonary carcinoma cells. Data represent the means±SE and the results are expressed as a percentage of cell survival of treated cells compared to untreated cells;

FIG. 7 shows the effects of sMTf-derived peptides on in vivo angiogenesis. Matrigel plug assays were performed using nude mice as described in the Materials and Method section. Effect of the peptides of SEQ ID NOs: 5, 7, 9, 13 and 15 on matrigel implant neovascularization. Data represent the means±SE and the results are expressed in µg Hemoglobin/mg of dried sample. Statistically significant differences, as compared to respective control conditions, are indicated by * $p \leq 0.05$,  $p \leq 0.01$, * $p \leq 0.001$ (ANOVA; N=5)

FIG. 8 shows the amino acid sequence of human soluble melanotransferrin polypeptide (SEQ ID NO: 1, NCBI Reference Sequence: NP_005920.2);

FIG. 9 shows a sequence alignment of the two transferrin regions of human soluble melanotransferrin (residues 23-355 and 367-706). The portions corresponding to residues 210-229 and 556-575 are underlined. The sequence alignment was performed using the BLASTP 2.2.25+ program (Stephen F. Altschul et al., Nucleic Acids Res. 25:3389-3402; Stephen F. Altschul et al., FEBS J. 272:5101-5109).

FIGS. 10A and 10B show the nucleic acid sequence encoding human soluble melanotransferrin polypeptide (SEQ ID NO: 30, NCBI Reference Sequence: NM_005929.5). Coding sequence: 115-2331; Signal peptide: 115-171; Mature peptide 172-2328.

DISCLOSURE OF INVENTION

Figure 1A:
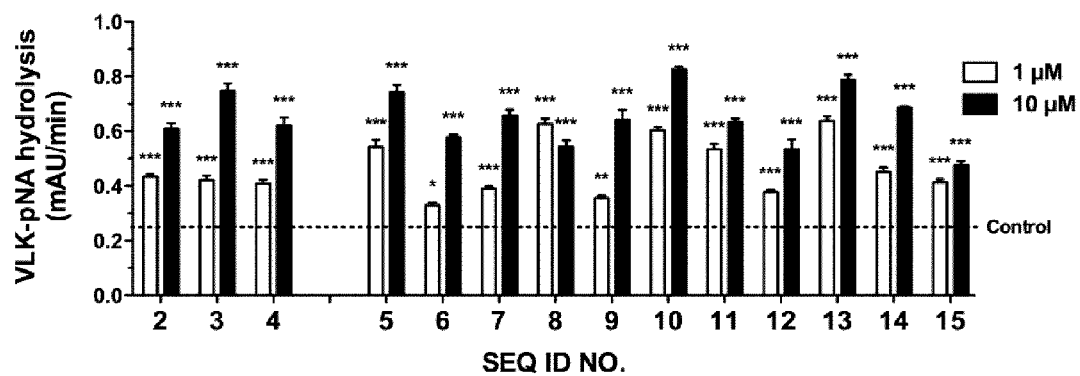
FIGS. 1A and 1B show the effect of soluble melanotransferrin (sMTf)-derived peptides on the plasminogen activation by urokinase-type plasminogen activator (uPA).

In the studies described herein, the present inventors have shown that peptides derived from human melanotransferrin, and more particularly from portions corresponding to residues 210-229 and 556-575 of the human melanotransferrin polypeptide of SEQ ID NO:1, stimulate plasminogen activation by urokinase-type plasminogen activator and in turn modulate angiogenesis and cell migration. Melanotransferrin (MTf), or melanoma-associated tumor antigen p97, is a membrane-bound glycoprotein that is a homolog of the transferrin (Tf) family of non-heme Fe-binding proteins (Brown et al., Nature 296: 171-173, 1982). MTf is a polypeptide of 738 amino acids (FIG. 8, SEQ ID NO:1) comprising a signal peptide (residues 1 to 19) and two transferrin regions (about residues 23-355 and 367-706) that exhibit significant sequence identity/similarity (48% identity, 65% similarity, FIG. 9). MTf was one of the first cell-surface markers associated with melanoma (Brown et al., J Immunol 127: 539-546, 1981). In fact, it was previously described as an oncofetal antigen, being expressed in only small quantities in normal tissues, but in much larger amounts in neoplastic cells (especially malignant melanoma cells) and fetal tissues (Woodbury et al., Proc Natl Acad Sci USA 77: 2183-2187, 1980; Brown et al., Proc Natl Acad Sci USA 78: 539-543, 1981). Two forms of p97 have been reported, one of which is bound to cell membranes by a glycosylphosphatidylinositol (GPI) anchor while the other form is both soluble and actively secreted.

Accordingly, in a first aspect, the present invention provides a peptide compound that increases plasminogen activation by urokinase-type plasminogen activator (uPA), said peptide compound comprising a domain comprising a sequence derived from residues 210-229 or 556-575 of the polypeptide of SEQ ID NO: 1. The peptide compound provided by the present invention does not contain the full length polypeptide sequence of SEQ ID NO: 1. The phrase "derived from residues 210-229 or 556-575 of the polypeptide of SEQ ID NO: 1" refers to a sequence having significant sequence identity or similarity with amino acids within the regions corresponding to 210-229 and/or 556-575 of SEQ ID NO: 1. Sequence identity refers to the degree of correspondence between two sequences, or the fraction of amino acids that are the same between two aligned sequences. Sequence similarity refers to the degree of resemblance between two sequences when they are compared, which is be calculated using a suitable similarity matrix, such as the PAM matrix or the BLOSUM matrix. In an embodiment, the sequence has at least 50% similarity or identity with a sequence of 15 consecutive amino acids or more of the regions corresponding to 210-229 and/or 556-575 of SEQ ID NO: 1. In further embodiments, the sequence has at least 55, 60, 65, 70, 75, 80, 85 or 90% similarity or identity with a sequence of 15 consecutive amino acids or more of the regions corresponding to 210-229 and/or 556-575 of SEQ ID NO: 1. Thus, the domain comprising a sequence derived from residues 210-229 or 556-575 of the polypeptide of SEQ ID NO:1 includes domains with altered sequences containing substitutions (preferably with functionally equivalent amino acid residues, naturally or non-naturally-occurring), relative to the native residues 210-229 or 556-575 of SEQ ID NO: 1, and which retain the biological activity of native human soluble melanotransferrin, notably the ability to increase plasminogen activation by urokinase-type plasminogen activator (uPA). For example, one or more amino acid residues within the sequence can be substituted by another amino acid having similar physico-chemical properties (e.g., similar polarity, charge, bulkiness, hydrophobicity and/or hydrophilicity) which acts as a functional equivalent, resulting in a silent alteration. Substitution for an amino acid within the sequence may be selected from other members of the class to which the amino acid belongs. For example, the positively charged (basic) amino acids include, arginine, lysine and histidine (as well as homoarginine and ornithine). The nonpolar (hydrophobic) amino acids include, leucine, isoleucine, alanine, phenylalanine, valine, proline, tryptophane and methionine. The uncharged polar amino acids include serine, threonine, cysteine, tyrosine, asparagine and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. In embodiments, the domain comprises a sequence that is at least 50%, 55, 60, 65, 70, 75, 80, 85, 90, 95, 96, 97, 98, 99 or 100% similar to a native sequence corresponding to residues 210-229 or 556-575 of the polypeptide of SEQ ID NO: 1. In embodiments, the domain comprises a sequence that is at least 50, 55, 60, 65, 70, 75, 80, 85, 90, 95, 96, 97, 98, 99 or 100% identical or similar to a native sequence corresponding to residues 210-229 or 556-575 of the polypeptide of SEQ ID NO: 1. Percent similarity and identity may be determined, for example, using well known algorithms and software. Optimal alignment of sequences for comparisons of identity/similarity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information.

In an embodiment, the domain comprises at least 5, 6, 7, 8, 9, 10, 11, 12, 13, 14 or 15 amino acids (contiguous or not) corresponding to residues 210-229 or 556-575 of the polypeptide of SEQ ID NO: 1.

In an embodiment, the above-mentioned domain is a domain of formula I:

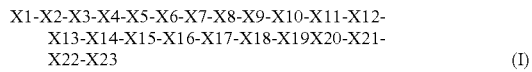

X1-X2-X3-X4-X5-X6-X7-X8-X9-X10-X11-X12-X13-X14-X15-X16-X17-X18-X19X20-X21-X22-X23    (I)

wherein
"-" is a bond;
X1 is an aromatic residue or is absent;
X2 is a basic residue, Ser, D-Ser or is absent;
X3 is Gly or is absent;
X4 is Ala, D-Ala or is absent;
X5 is an aromatic residue;
X6 is a basic amino acid;
X7 is Cys, D-Cys, Met, D-Met, Leu or D-Leu;
X8 is Leu, or D-Leu;
X9 is Val, D-Val, Ala or D-Ala;
X10 is an acidic residue;
X11 is Asn, D-Asn, Gln, D-Gln or Gly;
X12 is a basic residue, Ala or D-Ala;
X13 is Pro, D-Pro or Gly;
X14 is an acidic residue;
X15 is Val or D-Val;
X16 is Ala, D-Ala, Pro, D-Pro, Lys, D-Lys or Gly;
X17 is an aromatic residue;
X18 is Val or D-Val;
X19 is a basic residue, Thr or D-Thr;
X20 is a basic residue;
X21 is a basic residue, an acidic residue, Ile, D-Ile, or is absent;
X22 is a basic residue or is absent; and
X23 is a basic residue, an aromatic residue or is absent;

In a further aspect, there is provided a peptide compound comprising a domain of formula I as defined herein.

The term "peptide compound" refers to peptides, peptide analogs and peptidomimetics (or peptide mimetics) that comprise amino acid residues and that exhibit a biological activity, such as the ability to increase plasminogen activation by urokinase-type plasminogen activator (uPA), which may be measured using methods known in the art (see Example 1 below). Peptide analogs are commonly used in the pharmaceutical art as non-peptide drugs with properties analogous to those of a "template" peptide. The peptide analogs/peptidomimetics replicate the backbone geometry and physicochemical properties of biologically active peptides. Peptidomimetics that are structurally related to biologically active peptides may be used to produce an equivalent or enhanced biological activity (e.g., enhanced therapeutic and/or prophylactic effect). Generally, peptidomimetics are structurally similar to the template peptide, i.e. a peptide that has biological or pharmacological activity and that comprises naturally-occurring amino acids, but have one or more peptide linkages optionally replaced by linkages such as —CH$_2$NH—, —CH$_2$S—, —CH$_2$—CH$_2$—, —CH=CH— (cis and trans), —CH$_2$SO—, —CH(OH)CH$_2$—, —COCH$_2$— etc., by methods well known in the art (Spatola, Peptide Backbone Modifications, *Vega Data*, 1(3):267 (1983)); Spatola et al. (*Life Sci.* 38:1243-1249 (1986)); Hudson et al. (*Int. J. Pept. Res.* 14:177-185 (1979)); and Weinstein. B., 1983, Chemistry and Biochemistry, of Amino Acids, Peptides and Proteins, Weinstein eds, Marcel Dekker, New-York). Such peptidomimetics may have certain advantages including more economical production, greater chemical stability, enhanced pharmacological properties (e.g., half-life, absorption, potency, efficiency, etc.), reduced antigenicity and others. Peptidomimetic compounds can be obtained using any of the numerous approaches in combinatorial library methods known in the art. Accordingly, in an embodiment, one or more of the bond(s) ("-") is/are not a peptide bond/linkage. In another embodiment, all the bonds "-" are peptide bonds/linkages.

The term "residues" or "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc. Other amino acids include for example non-genetically encoded form of amino acid, as well as a conservative substitution of an L-amino acid. Naturally-occurring non-genetically encoded amino acids and synthetic amino acids include beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Harg), N-acetyl lysine, 2-amino butyric acid, 2-amino butyric acid, 2,4-diaminobutyric acid (D- or L-), p-aminophenylalanine, N-methylvaline, homocysteine, homoserine, cysteic acid, epsilon-amino hexanoic acid, delta-amino valeric acid, or 2,3-diaminobutyric acid (D- or L-), etc. These amino acids are well known in the art of biochemistry/peptide chemistry.

Synthetic amino acids providing similar side chain functionality can also be introduced into the peptide/domain. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, isobutyl, and iso-pentyl.

Non-carboxylate amino acids can be made to possess a negative charge, as provided by phosphono- or sulfated (e.g., —SO$_3$H) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine (NH$_2$) functionality. Yet other substitutions include nitrile derivatives (e.g., containing a CN-moiety in place of the CONH$_2$ functionality) of asparagine or glutamine, and sulfoxide derivative of methionine. In addition, any amide linkage in the peptide/domain may be replaced by a ketomethylene, hydroxyethyl, ethyl/reduced amide, thioamide or reversed amide moieties, (e.g., (—C=O)—CH$_2$—, (CHOH) CH$_2$, (CH$_2$—CH$_2$—), (—C=S)—NH—, or —NH—(—C=O) for (—C=O)—NH—).

Other modifications are also included within the definition of peptide compound of the present invention. For example, the size of the peptide/domain can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, keto-methylene pseudopeptides, β-turn dipeptide cores and β-aminoalcohols for these purposes are known to peptide chemists and are described in for example Peptidomimetic protocols (Methods in molecular medicine Vol. 23) W. M. Kazmierski (ed.), Humana Press and Advances in Amino Acid Mimetics and Peptidomimetics, Vols. 1 & 2, A. Abell (Ed).

The above-mentioned domain or peptide compound may comprise all L-amino acids, all D-amino acids or a mixture of L- and D-amino acids. In an embodiment, the above-mentioned domain or peptide compound comprises at least one D-amino acid. In an embodiment, said at least one D-amino acid is located in the N-terminal and/or C-terminal portion of the domain or peptide compound (e.g., within the last 2 or 3 N- and/or C-terminal residues). The presence of one or more D-amino acids typically results in peptides having increased stability (e.g., in vivo) due to decreased susceptibility to protease/peptidase cleavage, but which retain biological activity.

In embodiments, X1 is Tyr, D-Tyr or is absent; X2 is Arg, D-Arg, Ser, D-Ser or is absent; X4 is Ala or is absent; X5 is Phe or D-Phe; X6 is Arg or D-Arg; X7 is Cys, D-Cys, Met or D-Met; X10 is Glu or D-Glu; X11 is Asn, D-Asn or Gly; X12 is Arg, D-Arg, Ala or D-Ala; X13 is Gly; X14 is Asp or D-Asp; X17 is Phe or D-Phe; X19 is Arg, D-Arg, Lys, D-Lys, Thr or D-Thr; X20 is His, D-His, Arg or D-Arg; X21 is Lys, D-Lys, Glu, D-Glu, Ile, D-Ile, or is absent; X22 is Lys, D-Lys, Arg, D-Arg, or is absent; and/or X23 is Lys, D-Lys, Phe, D-Phe, or is absent.

In an embodiment, X1, X2, X3 and/or X4 is/are absent; in a further embodiment X1 to X4 are absent. In another embodiment, X21, X22 and/or X23 is/are absent; in a further embodiment X21 to X23 are absent.

In an embodiment, the above-mentioned domain is:

(a)

(SEQ ID NO: 16)
F-R-C-L-V-E-N-A-G-D-V-A-F-V-R-H;

-continued (b)

(SEQ ID NO: 17)
Y-S-G-A-F-R-C-L-A-E-G-A-G-D-V-A-F-V-K-H;

(c)

(SEQ ID NO: 18)
Y-R-G-A-F-R-C-L-V-E-N-A-G-D-V-A-F-V-R-H;

(d)

(SEQ ID NO: 19)
F-R-C-L-V-E-N-A-G-D-V-A-F-V-R-H-K-K-K;

(e)

(SEQ ID NO: 20)
F-R-C-L-V-E-N-A-G-D-V-G-F-V-R-H;

(f)

(SEQ ID NO: 21)
F-R-C-L-V-E-N-A-G-D-V-P-F-V-R-H;

(g)

(SEQ ID NO: 22)
F-R-C-L-V-E-Q-A-P-D-V-K-F-V-R-H-K-K-K;

(h)

(SEQ ID NO: 23)
Y-S-G-A-F-R-M-L-A-E-G-A-G-D-V-A-F-V-K-H-K-K-K;

(i)

(SEQ ID NO: 24)
•F-R-C-L-V-E-N-A-G-D-V-A-F-V-R-H-K-K-K ⟩K;
•F-R-C-L-V-E-N-A-G-D-V-A-F-V-R-H-K-K-K (j)

(SEQ ID NO: 25)
f-r-c-l-v-e-n-a-G-d-v-a-f-v-r-h-k-k-k;

(k)

(SEQ ID NO: 26)
F-R-C-L-V-E-N-R-G-D-V-P-F-V-R-H;

(l)

(SEQ ID NO: 27)
F-R-C-L-V-E-N-R-G-D-V-P-F-V-K-R-E-R-F;

(m)

(SEQ ID NO: 28)
Y-S-G-A-F-R-L-L-A-E-G-R-G-D-V-A-F-V-K-H-K-K; or (n)

(SEQ ID NO: 29)
F-R-C-L-V-E-N-R-G-D-V-P-F-V-T-R-I-R;

wherein f=D-Phe, r=D-Arg, c=D-Cys, l=D-Leu, v=D-Val, e=D-Glu, n=D-Asn, a=D-Ala, d=D-Asp, h=D-His, and k=D-Lys.

In embodiments, the above-mentioned domain is any combination of domains (a) to (n) defined above. In an embodiment, the above-mentioned domain is F-R-C-L-V-E-N-A-G-D-V-A-F-V-R-H (SEQ ID NO: 16). In another embodiment, the above-mentioned domain is Y-S-G-A F-R-C-L-A-E-G-A-G-D-V-A-F-V-K-H (SEQ ID NO: 17). In another embodiment, the above-mentioned domain is Y-R-G-A-F-R-C-L-V-E-N-A-G-D-V-A-F-V-R-H (SEQ ID NO: 18). In another embodiment, the above-mentioned domain is F-R-C-L-V-E-N-A-G-D-V-A-F-V-R-H-K-K-K (SEQ ID NO: 19). In another embodiment, the above-mentioned domain is F-R-C-L-V-E-N-A-G-D-V-G-F-V-R-H (SEQ ID NO: 20). In another embodiment, the above-mentioned domain is F-R-C-L-V-E-N-A-G-D-V-P-F-V-R-H (SEQ ID NO: 21). In another embodiment, the above-mentioned domain is F-R-C-L-V-E-Q-A-P-D-V-K-F-V-R-H-K-K-K (SEQ ID NO: 22). In another embodiment, the above-mentioned domain is Y-S-G-A-F-R-M-L-A-E-G-A-G-D-V-A-F-V-K-H-K-K-K (SEQ ID NO: 23). In another embodiment, the above-mentioned domain is (SEQ ID NO: 24)

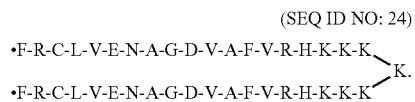

In another embodiment, the above-mentioned domain is f-r-c-l-v-e-n-a-G-d-v-a-f-v-r-h-k-k-k (SEQ ID NO: 25). In another embodiment, the above-mentioned domain is F-R-C-L-V-E-N-R-G-D-V-P-F-V-R-H (SEQ ID NO: 26). In another embodiment, the above-mentioned domain is F-R-C-L-V-E-N-R-G-D-V-P-F-V-K-R-E-R-F (SEQ ID NO: 27). In another embodiment, the above-mentioned domain is Y-S-G-A F-R-L-L-A-E-G-R-G-D-V-A-F-V-K-H-K-K (SEQ ID NO: 28). In another embodiment, the above-mentioned domain is F-R-C-L-V-E-N-R-G-D-V-P-F-V-T-R-I-R (SEQ ID NO: 29).

In an embodiment, the above-mentioned domain or peptide compound contains 100 amino acid residues or less, in a further embodiment 75 amino acid residues or less, in yet a further embodiment 50 amino acid residues or less. In an embodiment, the above-mentioned domain or peptide compound contains between about 8 residues to about 100 residues. In a further embodiment, the above-mentioned domain or peptide compound contains between about 10 residues to about 50 residues. In a further embodiment, the above-mentioned domain or peptide compound contains between about 10 residues to about 40 residues. In a further embodiment, the above-mentioned domain or peptide compound contains between about 11, 12, 13, 14 or 15 residues to about 25, 26, 27, 28, 29 or 30 residues. In a further embodiment, the above-mentioned peptide compound contains 11, 12, 13, 14, 15, 16, 17, 18, 19, 20, 21, 22, 23, 24, 25, 26, 27, 28, 29, or 30 residues.

Therefore, in embodiments, the above-mentioned peptide compound may comprise, further to the domain defined above, one more amino acids covalently linked to the amino- and/or carboxy-termini of said domain. The above-mentioned peptide compound may thus be a chimeric or fusion peptide containing a domain as described herein, linked at its amino- or carboxy-terminal end, or both, to an amino acid sequence of a different protein or peptide. In an embodiment, the above-mentioned peptide compound may comprise a peptide moiety for targeting the peptide compound to a particular cell, tissue and/or organ (e.g., a tumor).

In other embodiment, the peptide compound may comprise a two or more domains covalently linked to one another either directly or indirectly (through a spacer or linker).

In embodiments, the N- and/or C-terminal amino acids of the above-mentioned peptide compound or domain may be modified, for example by amidation, acetylation, acylation or any other modifications known in the art.

Accordingly, in another aspect, the present invention provides a peptide compound of formula (II)

Z1-X1-X2-X3-X4-X5-X6-X7-X8-X9-X10-X11-X12-X13-X14-X15-X16-X17-X18-X19-X20-X21-X22-X23-Z2 (I)

wherein X1 to X23 are as defined above;
Z1 is an amino-terminal modification or is absent; and
Z2 is a carboxy-terminal modification or is absent.

In an embodiment, the amino terminal residue (i.e., the free amino group at the N-terminal end) of the peptide compound is modified (e.g., for protection against degradation), for example by covalent attachment of a moiety/chemical group (Z1). In an embodiment, the amino-terminal modification (Z1) is a straight chained or branched alkyl group of 1 to 20 carbons (in embodiments 1 to 6, 8, 12 or 16 carbons), or an acyl group (R—CO—), wherein R is a hydrophobic moiety (e.g., an alkyl chain, such as acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In a further embodiment, Z1 is a sequence of one or more amino acids attached to X1. In another embodiment, Z1 is a targeting moiety.

In an embodiment, the carboxy terminal residue (i.e., the free carboxy group at the C-terminal end of the peptide) of the peptide compound is modified (e.g., a carboxy-terminal modifying group is attached via an ester linkage). Similar to N-terminal modifications, addition of chemical groups at the peptide C-terminal end may render the peptide compound less susceptible to degradation by peptidase and/or increase serum stability. In an embodiment, the C-terminal modifying group is an hydroxamate group, a nitrile group, an amide (primary, secondary or tertiary) group, an aliphatic amine of 1 to 10 carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In a further embodiment, $Z^2$ is an amide, more particularly $NH_2$. In a further embodiment, Z2 is a sequence of one or more amino acids. In another embodiment, Z2 is a targeting moiety.

The peptide compounds of the present invention may further comprise modifications that confer additional biological properties to the peptide compounds such as protease resistance, plasma protein binding, increased plasma half-life, intracellular penetration, etc. Such modifications include, for example, covalent attachment of fatty acids (e.g., $C_6$-$C_{18}$) to the peptide compound, attachment to proteins such as albumin (see, e.g., U.S. Pat. No. 7,268,113); glycosylation, biotinylation or PEGylation acetylation, acylation, addition of acetomidomethyl (Acm) group, ADP-ribosylation, alkylation, amidation, carbamoylation, carboxyethylation, esterification, covalent attachment of flavin, covalent attachment of a heme moiety, covalent attachment of a nucleotide or nucleotide derivative, covalent attachment of a drug, covalent attachment of a marker (e.g., a fluorescent or radioactive marker), covalent attachment of a lipid or lipid derivative, covalent attachment of phosphatidylinositol, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, and ubiquitination. Posttranslational modifications also include the addition of polymers to stabilize the peptide compound or to improve pharmacokinetics or pharmacodynamics. The above description of modification of the peptide compounds does not limit the scope of the approaches nor the possible modifications that can be engineered.

In embodiments, the above-mentioned peptide compound is:

(a)
(SEQ ID NO: 2)
Ac-F-R-C-L-V-E-N-A-G-D-V-A-F-V-R-H-NH₂;

(b)
(SEQ ID NO: 3)
Ac-Y-S-G-A-F-R-C-L-A-E-G-A-G-D-V-A-F-V-K-H-NH₂;

(c)
(SEQ ID NO: 4)
Ac-Y-R-G-A-F-R-C-L-V-E-N-A-G-D-V-A-F-V-R-H-NH₂;

(d)
(SEQ ID NO: 5)
Ac-F-R-C-L-V-E-N-A-G-D-V-A-F-V-R-H-K-K-K-NH₂;

(e)
(SEQ ID NO: 6)
Ac-F-R-C-L-V-E-N-A-G-D-V-G-F-V-R-H-NH₂;

(f)
(SEQ ID NO: 7)
Ac-F-R-C-L-V-E-N-A-G-D-V-P-F-V-R-H-NH₂;

(g)
(SEQ ID NO: 8)
Ac-F-R-C-L-V-E-Q-A-P-D-V-K-F-V-R-H-K-K-K-NH₂;

(h)
(SEQ ID NO: 9)
Ac-Y-S-G-A-F-R-M-L-A-E-G-A-G-D-V-A-F-V-K-H-K-K-K-NH₂;

(i)
(SEQ ID NO: 10)
Ac-F-R-C-L-V-E-N-A-G-D-V-A-F-V-R-H-K-K-K
                                              ⟩K-NH₂;
Ac-F-R-C-L-V-E-N-A-G-D-V-A-F-V-R-H-K-K-K (j)
(SEQ ID NO: 11)
Ac-f-r-c-l-v-e-n-a-G-d-v-a-f-v-r-h-k-k-k-NH₂;

(k)
(SEQ ID NO: 12)
Ac-F-R-C-L-V-E-N-R-G-D-V-P-F-V-R-H-NH₂;

(l)
(SEQ ID NO: 13)
Ac-F-R-C-L-V-E-N-R-G-D-V-P-F-V-K-R-E-R-F-NH₂;

(m)
(SEQ ID NO: 14)
Ac-Y-S-G-A-F-R-L-L-A-E-G-R-G-D-V-A-F-V-K-H-K-K-K-NH₂; or (n)
(SEQ ID NO: 15)
Ac-F-R-C-L-V-E-N-R-G-D-V-P-F-V-T-R-I-R-NH₂;

wherein Ac=acetyl, f=D-Phe, r=D-Arg, c=D-Cys, l=D-Leu, v=D-Val, e=D-Glu, n=D-Asn, a=D-Ala, d=D-Asp, h=D-His, and k=D-Lys, or a salt thereof.

In embodiments, the above-mentioned peptide compound is any combination of peptide compounds (a) to (n) defined above. In an embodiment, the above-mentioned peptide compound is Ac-F-R-C-L-V-E-N-A-G-D-V-A-F-V-R-H-NH₂ (SEQ ID NO: 2). In another embodiment, the above-mentioned peptide compound is Ac-Y-S-G-A F-R-C-L-A-E-G-A-G-D-V-A-F-V-K-H-NH₂ (SEQ ID NO: 3). In another embodiment, the above-mentioned peptide compound is Ac-Y-R-G-A-F-R-C-L-V-E-N-A-G-D-V-A-F-V-R-H-NH₂ (SEQ ID NO: 4). In another embodiment, the above-mentioned peptide compound is Ac-F-R-C-L-V-E-N-A-G-D-V-A-F-V-R-H-K-K-K-NH₂ (SEQ ID NO: 5). In another embodiment, the above-mentioned peptide compound is Ac-F-R-C-L-V-E-N-A-G-D-V-G-F-V-R-H-NH₂ (SEQ ID NO: 6). In another embodiment, the above-mentioned peptide compound is Ac-F-R-C-L-V-E-N-A-G-D-V-P-F-V-R-H-NH₂ (SEQ ID NO: 7). In another embodiment, the above-mentioned peptide compound is Ac-F-R-C-L-V-E-Q-A-P-D-V-K-F-V-R-H-K-K-K-NH₂ (SEQ ID NO: 8). In another embodiment, the above-mentioned peptide compound is Ac-Y-S-G-A-F-R-M-L-A-E-G-A-G-D-V-A-F-V-K-H-K-K-K-NH₂ (SEQ ID NO: 9). In another embodiment, the above-mentioned peptide compound is (SEQ ID NO: 10)
Ac-F-R-C-L-V-E-N-A-G-D-V-A-F-V-R-H-K-K-K
                                              ⟩K-NH₂.
Ac-F-R-C-L-V-E-N-A-G-D-V-A-F-V-R-H-K-K-K In another embodiment, the above-mentioned peptide compound is Ac-f-r-c-l-v-e-n-a-f-v-r-h-k-k-k-NH₂ (SEQ ID NO: 11). In another embodiment, the above-mentioned peptide compound is Ac-F-R-C-L-V-E-N-R-G-D-V-P-F-V-R-H-NH₂ (SEQ ID NO: 12). In another embodiment, the above-mentioned peptide compound is Ac-F-R-C-L-V-E-N-R-G-D-V-P-F-V-K-R-E-R-F-NH₂ (SEQ ID NO: 13). In another embodiment, the above-mentioned peptide compound is Ac-Y-S-G-A F-R-L-L-A-E-G-R-G-D-V-A-F-V-K-H-K-K-NH₂ (SEQ ID NO: 14). In another embodiment, the above-mentioned peptide compound is Ac-F-R-C-L-V-E-N-R-G-D-V-P-F-V-T-R-I-R-NH₂ (SEQ ID NO: 15).

In embodiments, the above-mentioned peptide compound is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or separately prepared by reacting a free base function with a suitable acid. Many of the peptide compounds disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

The peptide compounds of the invention may be produced by expression in a host cell comprising a nucleic acid encoding the peptide compound (recombinant expression) or by chemical synthesis (e.g., solid-phase peptide synthesis). Peptides can be readily synthesized by manual and automated solid phase procedures well known in the art. Suitable syntheses can be performed by utilizing "t-Boc" or "Fmoc" procedures. Techniques and procedures for solid phase synthesis are described in for example Solid Phase Peptide Synthesis: A Practical Approach, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985.

Peptides and peptide analogs comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation, etc.) using methods well known in the art. Therefore, in embodiments, in cases where a peptide compound described herein contains naturally occurring amino acids encoded by the genetic code, the peptide compound may be produced using recombinant methods, and may in embodiments be subjected to for example the just-noted modifications (e.g., acylation, amidation). Accordingly, in another aspect, the invention further provides a nucleic acid encoding the above-mentioned domain or peptide compound. The invention also provides a vector comprising the above-mentioned nucleic acid. In yet another aspect, the present invention provides a cell (e.g., a host cell) comprising the above-mentioned nucleic acid and/or vector.

The invention further provides a recombinant expression system, vectors and host cells, such as those described above, for the expression/production of a peptide compound of the invention, using for example culture media, production, isolation and purification methods well known in the art.

The peptide compounds of the invention can be purified by many techniques of peptide purification well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may for example be used.

In an embodiment, the above-mentioned peptide compound is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc.

In another aspect, the present invention provides a composition (e.g., a pharmaceutical composition) comprising the above-mentioned peptide compound. In an embodiment, the composition further comprises one or more pharmaceutically acceptable carriers, excipients, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "pharmaceutically acceptable carriers, excipients, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like (see, e.g., Rowe et al., *Handbook of Pharmaceutical Excipients*, Pharmaceutical Press; 6$^{th}$ edition, 2009).

The peptide compound of the present invention may be formulated for administration via any conventional route, such as intravenous, oral, transdermal, intraperitoneal, subcutaneous, mucosal, intramuscular, intranasal, intrapulmonary, parenteral or topical administration. The preparation of such formulations is well known in the art (see, e.g., *Remington: The Science and Practice of Pharmacy*, Lippincott Williams & Wilkins; 21$^{st}$ edition, 2005).

The peptide compound of the present invention may be useful for inhibition angiogenesis and/or cell migration, for example for preventing and/or treating a disease/condition associated with abnormal angiogenesis and/or cell migration (e.g., diseases/conditions in which inhibition or reduction of angiogenesis would be beneficial). As used herein, "abnormal angiogenesis" refers to abnormal growth of new blood vessels. Examples of diseases/conditions associated with abnormal angiogenesis include age-related macular degeneration, diabetic retinopathy, premature infant retinopathies, hemangiomas, psoriasis, arthritis, chronic inflammation, atherosclerosis, tumor growth and/or metastasis (e.g., cancer).

Accordingly, in another aspect, the present invention provides a method of inhibiting angiogenesis and/or cell migration in a subject comprising administering an effective amount of the above-mentioned peptide compound or the above-mentioned pharmaceutical composition, to a subject in need thereof.

In another aspect, the present invention provides a method of treating cancer comprising administering an effective amount of the above-mentioned peptide compound or the above-mentioned pharmaceutical composition, to a subject in need thereof.

In another aspect, the present invention provides a use of the above-mentioned peptide compound or the above-mentioned pharmaceutical composition for inhibiting angiogenesis and/or cell migration in a subject.

In another aspect, the present invention provides a use of the above-mentioned peptide compound or the above-mentioned pharmaceutical composition for the manufacture of a medicament for inhibiting angiogenesis and/or cell migration in a subject.

In another aspect, the present invention provides a use of the above-mentioned peptide compound or the above-mentioned pharmaceutical composition for treating cancer in a subject.

In another aspect, the present invention provides a use of the above-mentioned peptide compound or the above-mentioned pharmaceutical composition for the manufacture of a medicament for treating cancer in a subject.

In another aspect, the present invention provides the above-mentioned peptide compound or the above-mentioned pharmaceutical composition, for use as a medicament. In an embodiment, the above-mentioned medicament is for inhibiting angiogenesis and/or cell migration in a subject. In another embodiment, the above-mentioned medicament is for the treatment of cancer in a subject.

In another aspect, the present invention provides the above-mentioned peptide compound or the above-mentioned pharmaceutical composition for inhibiting angiogenesis and/or cell migration in a subject.

In another aspect, the present invention provides the above-mentioned peptide compound or the above-mentioned pharmaceutical composition for the manufacture of a medicament for inhibiting angiogenesis and/or cell migration in a subject.

In another aspect, the present invention provides the above-mentioned peptide compound or the above-mentioned pharmaceutical composition for treating cancer in a subject.

In another aspect, the present invention provides the above-mentioned peptide compound or the above-mentioned pharmaceutical composition for the manufacture of a medicament for treating cancer in a subject.

In an embodiment, the above-mentioned cancer is melanoma, prostate cancer, leukemia, hormone dependent cancer, breast cancer, colon cancer, lung cancer, skin cancer, ovarian cancer, pancreatic cancer, bone cancer, liver cancer, biliary cancer, lymphoma, sarcoma, esophageal cancer, stomach cancer, brain cancer, kidney cancer or epidermal cancer.

In an embodiment, the cancer or tumor cells express melanotransferrin (p97) at their surface.

In another embodiment, the above-mentioned peptide compound or pharmaceutical composition prevents, inhibits or reduces metastasis.

An "effective amount" refers to an amount effective, at dosages and for periods of time necessary, to achieve the desired biological activity (e.g. stimulating plasminogen activation by urokinase-type plasminogen activator, modulating angiogenesis and/or cell migration) and/or the prophylactic/therapeutic result (e.g., prevention and/or treatment of the diseases/disorders noted above). A "therapeutically effective amount" refers to an effective amount in the context of therapy; a "prophylactically effective amount" refers to an effective amount in the context of prophylaxis. An effective amount of a compound of the invention may vary according to factors such as the disease state, age, sex, and weight of the individual, and the ability of the compound to elicit a desired response in the individual. Dosage regimens may be adjusted to provide the optimum prophylactic/therapeutic response. An effective amount is also one in which any toxic or detrimental effects of the compound are outweighed by the prophylactic/therapeutic beneficial effects. For any particular subject, specific dosage regimens may be adjusted over time according to the individual need and the professional judgment of the person administering or supervising the administration of the compositions. In an embodiment, the peptide compound is administered at a daily dose of about 0.1 mg to about 20 mg, in a further embodiment of about 0.5 mg to about 20 mg, in a further embodiment at a daily dose of about 1 mg to about 20 mg.

The terms "treatment", "treating" and the like are intended to mean obtaining a desired pharmacologic and/or physiologic effect, e.g., inhibiting tumor growth, metastasis. The effect may be prophylactic in terms of completely or partially preventing a disease or symptom thereof (preventing metastasis) and/or may be therapeutic in terms of a partial or complete cure for a disease and/or adverse effect attributable to the disease. "Treatment" as used herein relates to any treatment of a disease in a mammal, particularly a human, and includes inhibiting the disease/condition, arresting or slowing the development/progression of the disease; or relieving the disease (e.g., reducing symptoms associated with the disease).

In an embodiment, the peptide compound of the present invention is indirectly administered to the subject, for example by administering to a subject a nucleic acid encoding the peptide compound, or a vector comprising a nucleic acid encoding the peptide compound, or a cell comprising the nucleic acid or vector, so that the peptide is produced in vivo following administration to the subject. Nucleic acids may be delivered to cells in vivo using methods well known in the art such as direct injection of DNA, receptor-mediated DNA uptake, viral-mediated transfection or non-viral transfection and lipid based transfection, all of which may involve the use of gene therapy vectors.

In an embodiment, the above-mentioned prevention and/or treatment comprises administration of the above-mentioned peptide compounds or pharmaceutically acceptable salts thereof or pharmaceutical compositions, in combination with one or more additional active/therapeutic agents, or in combination with any other therapy. The combination of prophylactic/therapeutic agents and/or compositions may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question. Accordingly, in an embodiment, the peptide compounds are administered/used in combination with an anti-cancer therapy, for example a chemotherapeutic agent, an angiogenesis inhibitor, hormonal therapy, radiation therapy, photodynamic therapy, surgery, immunotherapy, vaccine or transplantation.

As used herein, the terms "subject" or "patient" are taken to mean warm blooded animals such as mammals, for example, cats, dogs, mice, guinea pigs, horses, bovine cows, sheep and humans. In an embodiment, the subject is a mammal. In a further embodiment, the above-mentioned subject is a human.

MODE(S) FOR CARRYING OUT THE INVENTION

The present invention is illustrated in further details by the following non-limiting examples.

ABBREVIATIONS

DMF: N,N-Dimethylformamide
DIEA: Diisopropylethylamine
COMU: (1-Cyano-2-ethoxy-2-oxoethylidenaminooxy)dimethylamino-morpholino-carbenium hexafluorophosphate
TFA: Trifluoroacetic acid
MALDI-TOF: Matrix Assisted Laser Desorption/Ionization Mass Spectrometry.
HPLC: High Performance Liquid Chromatography
BHA: Benzhydrylamine resin
Pbf: 2,2,4,6,7-Pentamethyldihydrobenzofurane-5-sulfonyl
Boc: t-Butoxycarbonyl
t-Bu: t-Butyl
Trt: Trityl
Ac: acetyl
a: D-alanine
r: D-arginine
f: D-phenylalanine
c: D-cysteine
l: D-leucine
v: D-valine
e: D-glutamic
n: D-asparagine
d: D-aspartic
h: D-histidine
k: D-lysine Throughout the instant application, naturally occurring amino acids are designated interchangeably using the one or three letter codes (see TABLE I below for correspondence between them).

TABLE I

| Amino acids, one and three letter codes | | |
|---|---|---|
| Amino acid | Three letter code | One letter code |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Example 1

Materials and Methods

Synthesis and Preparation of sMTf Fragments and Derivatives.

Solid phase synthesis: The sMTf peptides were made using a manual or automatic solid phase peptide synthesis approach using fluorenylmethoxycarbonyl-protected alpha-amino acids with appropriate side-chain protection and Benzhydrylamine (BHA) resin (BACHEM AG) with a loading of 0.75 mmol/g. Before the coupling of amino acids, 6-aminohexanoic acid and Rink linker were coupled to the resin, the Fmoc-[9H-fluoren-9-ylmethoxycarbonyl] protected amino acid were then coupled using [(1-Cyano-2-ethoxy-2-oxoethylidenaminooxy)dimethylamino-morpholino-carbenium hexafluorophosphate] (COMU) and diisopropylethylamine (DIEA) in N,N-Dimethylformamide (DMF) for 1 hour. Fmoc deprotection was performed using 20% (v/v) piperidine in DMF for 1 hour. A general procedure for N-capping the peptides of the invention with acetyl was performed using acetic anhydride and DIEA. After completion of synthesis, peptides were cleaved from the solid phase support with simultaneous side-chain deprotection. Crude linear peptides were further purified by preparative RP-HPLC on Vydac™ C18-columns using acetonitrile gradient in 0.1% Trifluoroacetic acid (TFA). The peptides were vacuum-dried to remove acetonitrile and lyophilized from 0.1% TFA. Purity was assessed by analytical High Performance Liquid Chromatography (HPLC) and masses were determined by Matrix Assisted Laser Desorption/ionisation Mass Spectromety (MALDI-TOF MS) analysis using a Voyager™ instrument (PerSeptive Biosystems Inc.). The sequences of the peptides used in the experiments described herein are depicted in Table II.

TABLE II

Sequences of the peptides used in the experiments described herein

| Code | Sequence |
|---|---|
| SEQ ID NO: 2<br>MTF(560-575) | Ac-F-R-C-L-V-E-N-A-G-D-V-A-F-V-R-H-NH$_2$ |
| SEQ ID NO: 3<br>MTF(210-229) | Ac-Y-S-G-A F-R-C-L-A-E-G-A-G-D-V-A-F-V-K-H-NH$_2$ |
| SEQ ID NO: 4<br>MTF(556-575) | Ac-Y-R-G-A-F-R-C-L-V-E-N-A-G-D-V-A-F-V-R-H-NH$_2$ |
| SEQ ID NO: 5 | Ac-F-R-C-L-V-E-N-A-G-D-V-A-F-V-R-H-K-K-K-NH$_2$ |
| SEQ ID NO: 6 | Ac-F-R-C-L-V-E-N-A-G-D-V-G-F-V-R-H-NH$_2$ |
| SEQ ID NO: 7 | Ac-F-R-C-L-V-E-N-A-G-D-V-P-F-V-R-H-NH$_2$ |
| SEQ ID NO: 8 | Ac-F-R-C-L-V-E-Q-A-P-D-V-K-F-V-R-H-K-K-K-NH$_2$ |
| SEQ ID NO: 9 | Ac-Y-S-G-A F-R-M-L-A-E-G-A-G-D-V-A-F-V-K-H-K-K-K-NH$_2$ |
| SEQ ID NO: 10 | Ac-F-R-C-L-V-E-N-A-G-D-V-A-F-V-R-H-K-K-K<br>                                                      \\<br>                                                      Lys-NH$_2$<br>                                                      /<br>Ac-F-R-C-L-V-E-N-A-G-D-V-A-F-V-R-H-K-K-K |
| SEQ ID NO: 11 | Ac-f-r-c-l-v-e-n-a-G-d-v-a-f-v-r-h-k-k-k-NH$_2$ |
| SEQ ID NO: 12 | Ac-F-R-C-L-V-E-N-R-G-D-V-P-F-V-R-H-NH$_2$ |
| SEQ ID NO: 13 | Ac-F-R-C-L-V-E-N-R-G-D-V-P-F-V-K-R-E-R-F-NH$_2$ |
| SEQ ID NO: 14 | Ac-Y-S-G-A F-R-L-L-A-E-G-R-G-D-V-A-F-V-K-H-K-K-NH$_2$ |
| SEQ ID NO: 15 | Ac-F-R-C-L-V-E-N-R-G-D-V-P-F-V-T-R-I-R-NH$_2$ |

Ac = acetyl, f = D-Phe, r = D-Arg, c = D-Cys, l = D-Leu, v = D-Val, e = D-Glu, n = D-Asn, a = D-Ala, d = D-Asp, h = D-His, and k = D-Lys In Vitro Plasminogen Activation by uPA.

The in vitro enzymatic activity of uPA was measured using a colorimetric assay. To study the effect of sMTf-derived peptides on plasminogen activation by uPA, the reaction was performed in plasminogen activation buffer (50 mM Tris/HCl (pH 7.5), 150 mM NaCl and 50 mM CaCl$_2$) in a final volume of 200 μL. This incubation medium also contained 30 nM plasminogen and 15 μg of the chromogenic plasmin substrate D-Val-Leu-Lys p-nitroanilide (VLK-pNA). The reaction was started by the addition of 1 ng of uPA. In this assay, the cleavage of VLK-pNA results in a p-nitroaniline molecule that absorbs at 405 nm. The reaction product was monitored at 37° C. during 3 hours every 2 minutes using a Microplate Thermomax™ Autoreader. The velocity of the VLK-pNA hydrolysis reaction was calculated and results are expressed in mAU/min.

In Vitro Cell Migration.

HMEC-1 and NCI-H460 cell migration was performed using Transwell filters (8 μm pore size) pre-coated with 0.15% gelatin for 2 hours at 37° C. or overnight at 4° C. The Transwell filters were washed once with PBS and assembled in 24-well plates. To study the effect of sMTf-derived peptides on cell migration, the lower chambers were filled with 300 μL of serum-free cell culture medium with or without various concentrations of peptides (2×). Next, HMEC-1 and NCI-H460 cells were harvested by trypsinization and centrifuged. Approximately 50 000 cells (HMEC-1) and 100 000 cells (NCI-H460) were resuspended in 100 μL of serum free medium and added into the upper chamber of each Transwell. Then, 400 μL of serum free medium were added into the lower chamber with or without various concentrations of peptides (2×). After 1 hour incubation, 300 μL of cell culture medium containing 20% serum were added in the lower chamber to stimulate cell migration (final peptide concentration 1×). The plates were then placed at 37° C. in 5% CO$_2$/95% air for 4 hours (HMEC-1) or 18 hours (NCI-H460). Cells that had migrated to the lower surface of the filters were fixed for 30 minutes with 10% formalin, stained 30 minutes with 0.1% crystal violet/20% MeOH, and washed twice with PBS. The cells on the upper side of the filters were removed mechanically by wiping with cotton swabs to remove all the cells that did not migrated. The cell migration was quantified in four fields per filters at 50× magnification using microscopy computer-assisted imaging (Northern Eclipse™ software). Results are expressed as a percentage of cell migration of treated cells compared to untreated cells.

Matrigel™ Plug Angiogenesis Assay.

Angiogenesis is considered to be indicated by the growth of blood vessels from subcutaneous tissue into a solid piece of Matrigel™. Specific pathogen-free, female Crl:CD-1®-nuBR nude mice were obtained from Charles River Laboratories (Lasalle, QC). All of the mice used were 5-10 weeks of age. Prior to injection, heparin was incubated with or without bFGF (250 ng/mL) and VEGF$_{165}$ (200 ng/mL) for 5 min, then 1 mL of MEM was added and the mixture diluted into phenol red-free Matrigel™ on ice for a final concentration of 12.4 μg/mL heparin. Then, specific pathogen-free, female Crl:CD-1®-nuBR nude mice were subcutaneously injected under anesthesia in the right flank with 0.5 mL of Matrigel™ alone or with Matrigel™ containing bFGF and VEGF. After 7 days, mice were sacrificed and Matrigel™ implants were harvested, washed with PBS and photographed. The remaining implants were immediately frozen and lyophilized overnight in order to evaluate the hemoglobin (Hb) concentrations. Testing of anti-angiogenic substances was initiated at the time of Matrigel™ implantation. Samples were then crushed and resuspended in 0.1% Triton™ X-100. Samples were mixed frequently for 1 h and centrifuged at 12,000×g for 15 min to remove particles. The concentration of hemoglobin (Hb) in the supernatant was then determined directly by measuring the absorbance at 405 nm and compared with a standard curve of purified Hb Hemoglobin content was expressed in μg Hb/mg of dried sample.

Xenograft Model Antitumor Assays.

For tumor cell inoculation in nude mice, U-87 MG or NCI-H460 cells were harvested by trypsinization using a trypsin/EDTA solution. Cells were washed two times with phosphate-buffered saline $Ca^{2+}$—$Mg^{2+}$ free (PBS-CMF) and centrifuged. The resulting pellet was resuspended in 1% methyl-cellulose in serum-free EMEM at a concentration of 2.5×10$^6$ cells per 100 μL. Specific pathogen-free, female Crl: CD-1®-nuBR nude mice were anesthetized by O$_2$/isoflurane inhalation and tumors were established by subcutaneous injection of 100 μL from cell suspension into the right flank. Tumors were measured in O$_2$/isoflurane anesthetized mice twice a week using a digital caliper and tumor volume was calculated as: π/6×length×width$^2$. When the first mouse from control group held a tumor reaching 1000 mm$^3$, tumors were photographed and mice from every group were sacrificed. Experiments were performed on 8 animals for each group. Recombinant sMTf treatment toxicity was evaluated by monitoring the body weight of control and treated mice, considering that a weight loss>20% results in a toxic effect.

Cell Toxicity.

sMTf-derived peptides cellular toxicity on HMEC-1 and NCI-H460 were performed using [methyl-$^3$H]-thymidine incorporation assay. To study the toxic effect of sMTf-derived peptides, HMEC-1 and NCI-H460 cells were harvested by trypsinization and centrifuged. Approximately 5000 cells (HMEC-1 and NCI-H460) were resuspended with 200 μL of fresh culture medium, seeded into white 96-well plate and placed at 37° C. in 5% CO$_2$/95% air. After 24 hours, the medium was removed and 200 μL of serum-free cell culture medium was added to synchronize the cells. After another 24 hours, the medium was removed and 200 μL of fresh complete medium with or without various peptide concentrations were added. After 24 hours incubation with the peptides, the medium was remove and 200 μL (0.5 μCi) of [methyl-$^3$H]-thymidine was added and placed at 37° C. in 5% CO$_2$/95% air for 4 hours. Then, the wells were gently washed twice with PBS at 37° C., incubated with 200 μL of EtOH:Acetic acid (3:1) for 10 minutes and dried under the hood. 50 μL of Microscint™-O was added per well, the plate was sealed, agitated for 3 minutes, and read on the microplate scintillation and luminescence counter (TopCount NXT, Packard). Results are expressed as a percentage of cell viability of treated cells compared to untreated cells.

Example 2

Effect of sMTf-Derived Peptides on the Plasminogen Activation by uPA

Figure 1B:
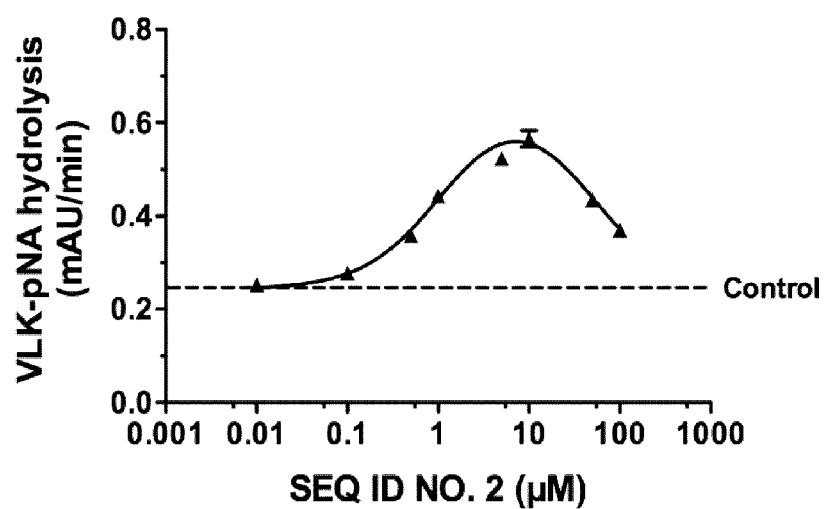

FIGS. 1A and 1B illustrate the stimulatory effect of sMTf-derived peptides on plasminogen activation by uPA and show that: (i) VLK-pNA hydrolysis by uPA increases when sMTf-derived peptides are added to the reaction at 1 and 10 μM (FIG. 1A); (and (ii) sMTf-derived peptide of SEQ ID NO:2 stimulates plasminogen cleavage by uPA in a dose-dependent manner (FIG. 1B).

Example 3

Effect of sMTf-Derived Peptides on Cellular Migration

Figure 2A:
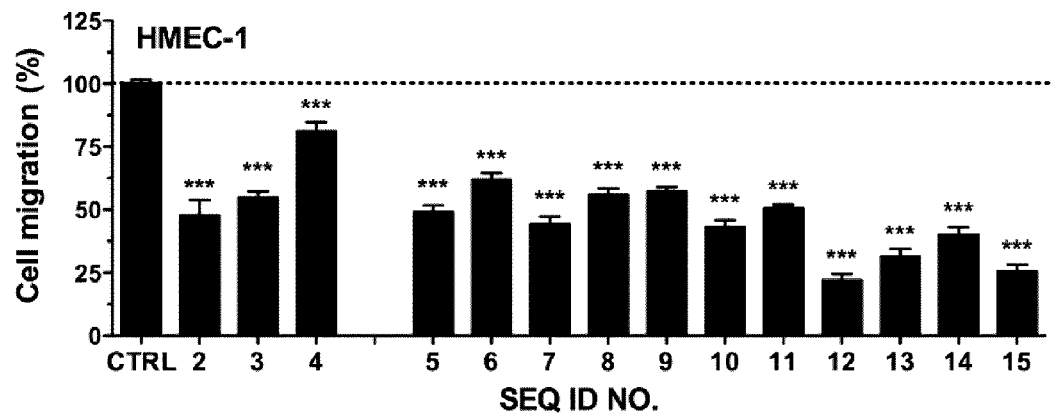
FIGS. 2A to 2D show the effect of sMTf-derived peptides on cellular migration. Cell migration was assessed using modified Boyden chambers as described in Example 1. Screening of the sMTf-derived peptides for their ability to inhibit cellular migration of HMEC-1 endothelial cells (FIG. 2A) and NCI-H460 pulmonary carcinoma cells (FIG. 2B). Cell migration was performed in the presence or absence (CTRL) of sMTf-derived peptides at 10 µM. HMEC-1 (FIG. 2C) and NCI-H460 (FIG. 2D) cell migration was measured in the presence or absence of various concentrations of sMTf-derived peptides (SEQ ID NOs: 2 [triangles], 13 [squares] or 15 [circles]). Data represent the means±SE and the results are expressed as a percentage of cell migration of treated cells compared to untreated cells. Statistically significant differences, as compared to control conditions, are indicated by * $p \leq 0.05$,  $p \leq 0.01$, * $p \leq 0.001$ (ANOVA; N=4)
Figure 2B:
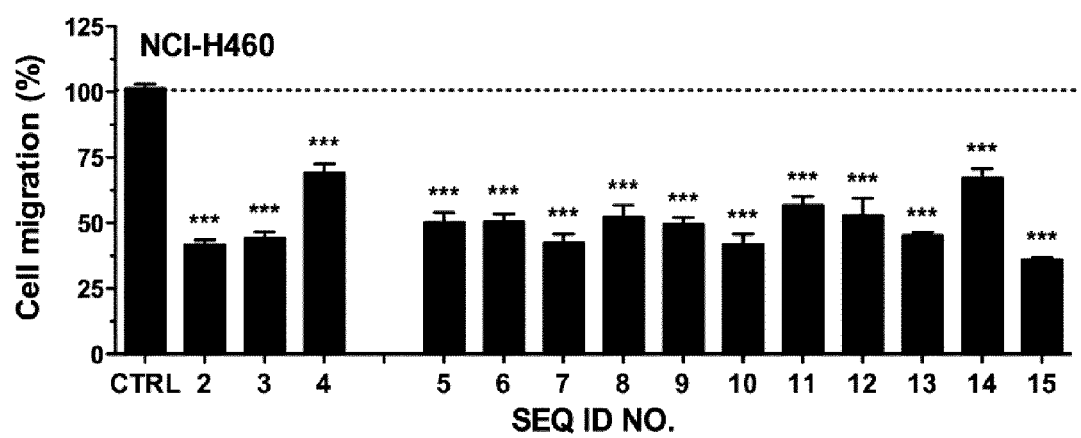
Figure 2C:
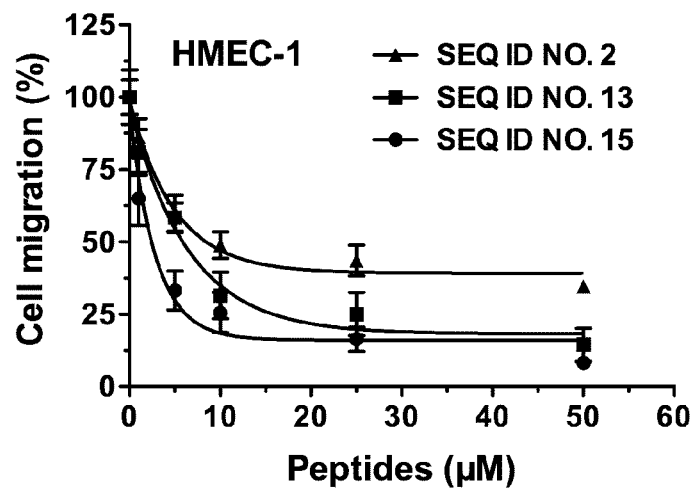
Figure 2D:
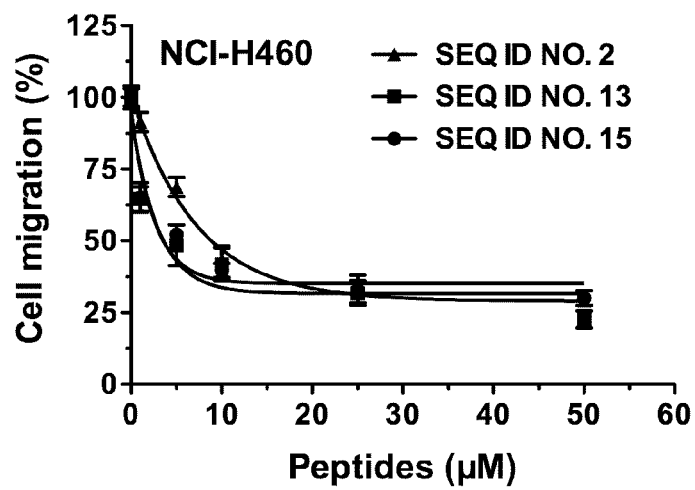

FIGS. 2A and 2B illustrate that sMTf-derived peptides inhibit the migration of HMEC-1 cells (FIG. 2A) and NCI-H460 cells (FIG. 2B) at 10 μM; sMTf-derived peptides of SEQ ID NOs: 2, 13 and 15 inhibit the migration of HMEC-1 cells (FIG. 2C) and NCI-H460 cells (FIG. 2D) in a dose-dependent manner.

Example 4

Effect of sMTf-Derived Peptides on Tumor Growth

Figure 3A:
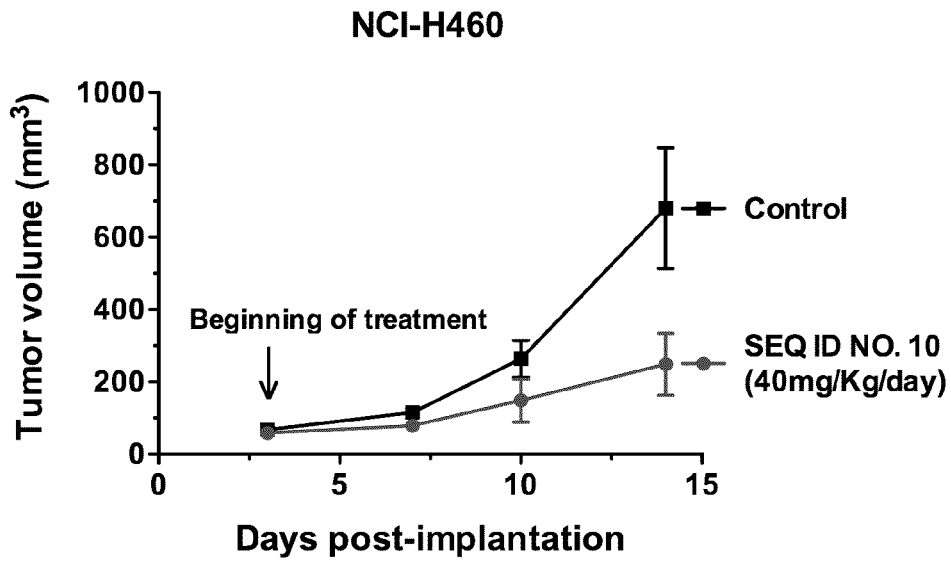
FIGS. 3A to 3C show the effect of sMTf-derived peptides on tumor growth (lung carcinoma). Human NCI-H460 lung carcinoma tumor xenograft was performed using nude mice as described in the Example 1.
Figure 3B:
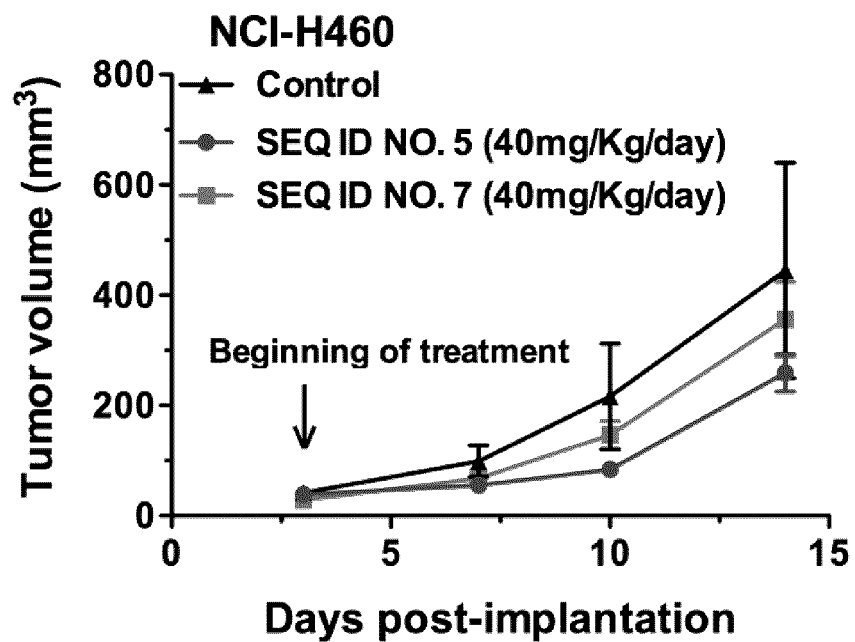
Figure 3C:
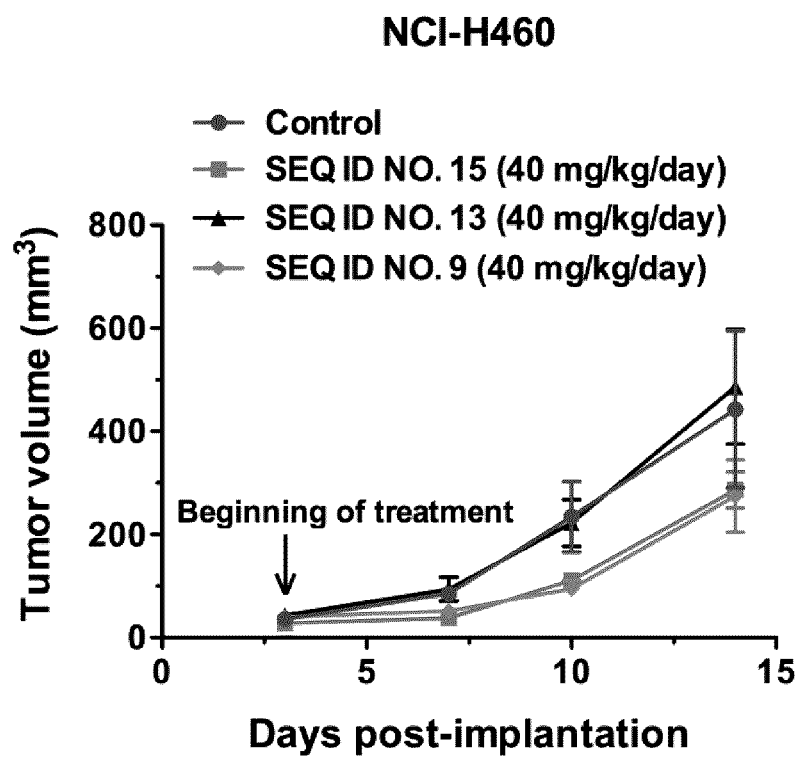

FIGS. 3A to 3C illustrate that sMTf-derived peptides of SEQ ID NO: 10 (FIG. 3A), SEQ ID NO: 5 (FIG. 3B), and SEQ ID NO: 9 (FIG. 3C) at 40 mg/Kg/day inhibit NCI-460 tumor growth.

Figure 4A:
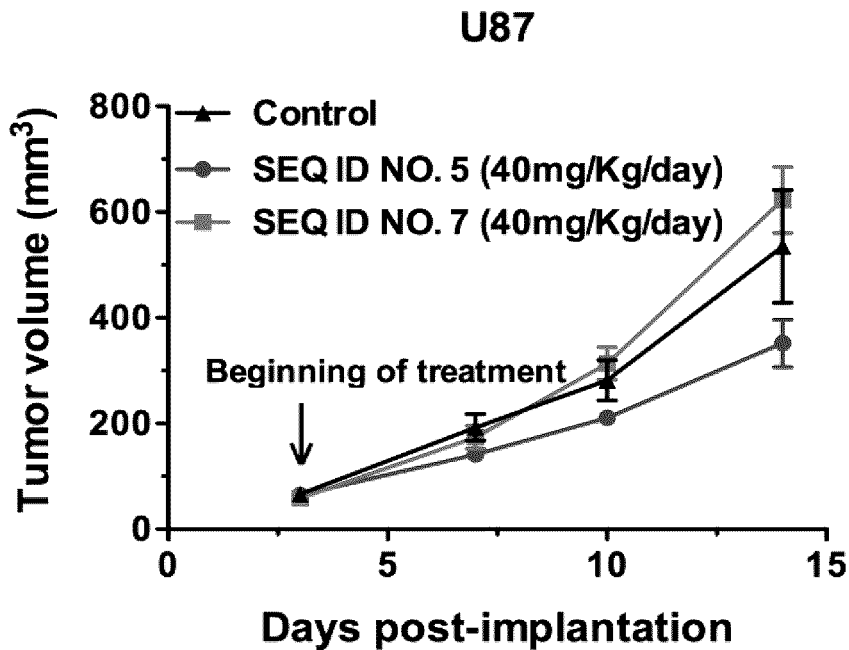
FIGS. 4A and 4B show the effect of sMTf-derived peptides on tumor growth (glioblastoma). Human U87 glioblastoma tumor xenograft was performed using nude mice as described in Example 1.
Figure 4B:
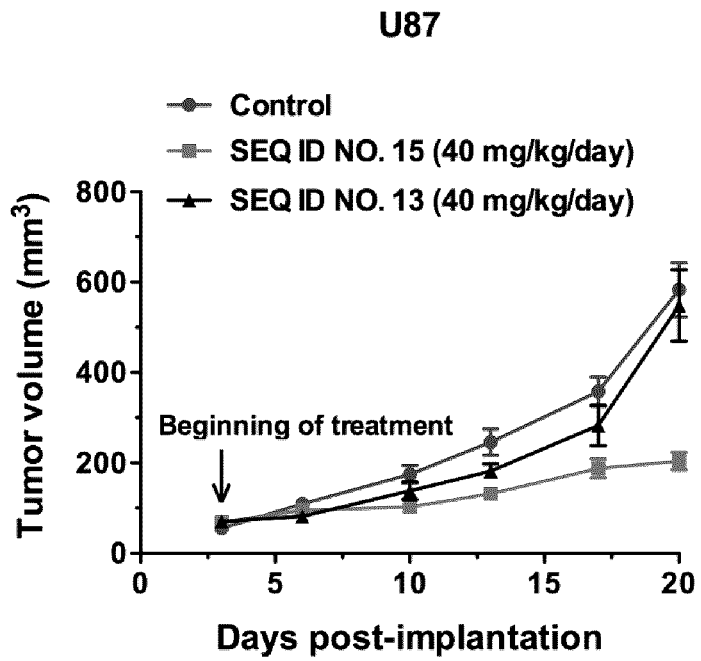

FIGS. 4A and 4B illustrate that sMTf-derived peptides of SEQ ID NO: 5 (FIG. 4A) and SEQ ID NO: 15 (FIG. 4B) at 40 mg/Kg/day inhibit U87 tumor growth.

Figures 5B, 6:
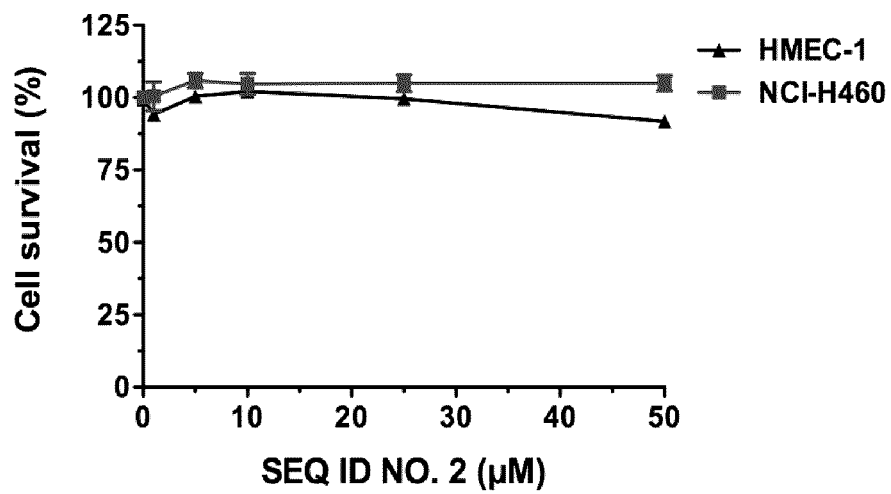

FIG. 5A illustrates that sMTf-derived peptides of SEQ ID NOs: 10, 5, 15 and 9 at 40 mg/Kg/day inhibit NCI-460 tumor growth by 69%, 45%, 37% and 42%, respectively; and FIG. 5B shows that SEQ ID NOs: 5 and 15 at 40 mg/Kg/day inhibit U87 tumor growth by 39% and 74%, respectively.

Example 5

Evaluation of the Cellular Toxicity of the sMTf-Derived Peptide of SEQ ID NO: 2

FIG. 6 illustrates that sMTf-derived peptide of SEQ ID NO: 2 do not demonstrate any cellular toxicity up to 50 μM on HMEC-1 and NCI-H460 cells.

Example 6

Effects of sMTf-Derived Peptides on In Vivo Angiogenesis

FIG. 7 illustrates that sMTf-derived peptide of SEQ ID NOs: 15, 13, 9, 5 and 7 inhibit in vivo neovascularisation induced by the growth factors FGF-2 and VEGF in a dose-dependent manner.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", an and the include corresponding plural references unless the context clearly dictates otherwise.

What is claimed is:

1. A compound that is (i) a peptide compound having the structure: Ac-F-R-C-L-V-E-N-R-G-D-V-P-F-V-K-R-E-R-F-NH$_2$ (SEQ ID NO: 13), wherein Ac=acetyl, or (ii) a pharmaceutically acceptable salt of (i).

2. A pharmaceutical composition comprising the compound of claim 1.

3. The pharmaceutical composition of claim 2, further comprising one or more pharmaceutically acceptable carriers, excipient, and/or diluents.

4. A method of inhibiting angiogenesis and/or cell migration in a subject comprising administering an effective amount of the compound of claim 1 to a subject in need thereof.

5. A method of inhibiting tumor growth and/or metastasis in a subject suffering from cancer comprising administering an effective amount of the compound of claim 1 to a subject in need thereof.

6. The method of claim 5, wherein said cancer is melanoma, prostate cancer, leukemia, hormone dependent cancer, breast cancer, colon cancer, lung cancer, skin cancer, ovarian cancer, pancreatic cancer, bone cancer, liver cancer, biliary cancer, lymphoma, sarcoma, esophageal cancer, stomach cancer, brain cancer, kidney cancer or epidermal cancer.

7. The method of claim 4, wherein the compound is administered intravenously, orally, transdermally, subcutaneously, mucosally, intramuscularly, intranasally, intrapulmonary, parenterally, intrarectally or topically.

8. The compound of claim 1, which is a peptide compound having the structure: Ac-F-R-C-L-V-E-N-R-G-D-V-P-F-V-K-R-E-R-F-NH$_2$ (SEQ ID NO: 13).

9. The compound of claim 1, which is a pharmaceutically acceptable salt of a peptide compound having the structure: Ac-F-R-C-L-V-E-N-R-G-D-V-P-F-V-K-R-E-R-F-NH$_2$ (SEQ ID NO: 13).

* * * * *